United States Patent
Diolez et al.

(10) Patent No.: US 10,653,668 B2
(45) Date of Patent: May 19, 2020

(54) COMPOUNDS FOR THE TREATMENT OF DISEASES LINKED TO MITOCHONDRIAL REACTIVE OXYGEN SPECIES (ROS) PRODUCTION

(71) Applicants: OP2 DRUGS, Pessac (FR); CENTRE HOSPITALIER UNIVERSITAIRE DE BOURDEAUX, Talence (FR); INSERM (INSTITUT NATIONAL DE LA SANTE ET DE LA RECHERCHE MEDICALE), Paris (FR); UNIVERSITE DE BORDEAUX, Bordeaux (FR)

(72) Inventors: Philippe Diolez, Pessac (FR); Dominique Detaille, Bordeaux (FR); Frédéric Marin, Paris (FR); Olivier Petitjean, Senlis (FR)

(73) Assignees: OP2 DRUGS, Pessac (FR); CENTRE HOSPITALIER UNIVERSITAIRE DE BOURDEAUX, Talence (FR); INSERM (INSTITUT NATIONAL DE LA SANTE ET DE LA RECHERCHE MEDICALE), Paris (FR); UNIVERSITE DE BORDEAUX, Bordeaux (FR)

( * ) Notice: Subject to any disclaimer, the term of this patent is extended or adjusted under 35 U.S.C. 154(b) by 0 days.

(21) Appl. No.: 16/368,040

(22) Filed: Mar. 28, 2019

(65) Prior Publication Data
US 2019/0274997 A1 Sep. 12, 2019

Related U.S. Application Data

(63) Continuation of application No. 15/758,519, filed as application No. PCT/EP2016/071170 on Sep. 8, 2016, now Pat. No. 10,272,066.

(60) Provisional application No. 62/215,215, filed on Sep. 8, 2015.

(30) Foreign Application Priority Data

Sep. 8, 2015 (EP) .................................... 15184217

(51) Int. Cl.
*A61K 31/385* (2006.01)
*A61P 9/10* (2006.01)
*A61P 3/10* (2006.01)
*A61K 31/497* (2006.01)

(52) U.S. Cl.
CPC .......... *A61K 31/385* (2013.01); *A61K 31/497* (2013.01); *A61P 3/10* (2018.01); *A61P 9/10* (2018.01)

(58) Field of Classification Search
None
See application file for complete search history.

(56) References Cited

FOREIGN PATENT DOCUMENTS

| WO | WO 98/27970 | 7/1998 |
|----|-------------|--------|
| WO | WO 01/09118 | 2/2001 |
| WO | WO 03/066058 | 8/2003 |
| WO | WO 03/068219 | 8/2003 |
| WO | WO 2008/106640 | 9/2008 |

OTHER PUBLICATIONS

Matsuo et al., CAS SciFinder abstract (database MEDLINE, Acc. No. 2000015882) of the Journal of Clinical Psychiatry (1999), 60(10), (letter) p. 706.*
Dansette et al., CAS SciFinder abstract (database CAPLUS, Acc. No. 1991:421375) of Advances in Experimental Medicine and Biology (1990), vol. 264, Issue: Antioxid. Ther. Prev. Med., pp. 209-215.*
Dansette et al., Advances in Experimental Medicine and Biology (1990), vol. 264, Issue: Antioxid. Ther. Prev. Med., pp. 209-215.*
Matsuo et al., The Journal of Clinical Psychiatry (1999), 60(10), (letter) p. 706.*
Giustarini et al., Biochemical Pharmacology (2014), 89(2), pp. 246-254.
H Nagayasu et al: "Inhibitory effects of malotilate on invasion and metastasis of rat mammary carcinoma cells by modifying the functions of vascular endothelial cells", British Journal of Cancer, vol. 77. No. 9, May 1, 1998 (May 1, 1998). pp. 1371-1377. XP055248150, GB ISSN: 0007-0920, 001: 10.1038/bjc.1998.229 abstract.

* cited by examiner

*Primary Examiner* — Brian J Davis
(74) *Attorney, Agent, or Firm* — Young & Thompson

(57) ABSTRACT

The present invention relates to the use of compounds for the prevention and treatment of diseases whose initiation and/or evolution relates to the production and effects of reactive oxygen species (ROS) of mitochondrial origin.

10 Claims, 17 Drawing Sheets

COMPOUNDS FOR THE TREATMENT OF DISEASES LINKED TO MITOCHONDRIAL REACTIVE OXYGEN SPECIES (ROS) PRODUCTION

FIELD OF INVENTION

The present invention relates to the use of compounds for the prevention and treatment of diseases whose initiation and/or evolution relate to the production and effects of reactive oxygen species (ROS) of mitochondrial origin.

BACKGROUND OF INVENTION

Mitochondrion is at the heart of the now widely acknowledged "free radical theory of ageing" and thus involved in the pathogenesis of nearly all ageing-associated diseases, including cardiovascular disease, neurodegenerative diseases (Parkinson's disease, Alzheimer's disease and the like), cancer and diabetes, as well as tissue dysfunctions of ischemic origin. This theory states that the accumulation of damages caused by reactive oxygen species (ROS) impacts numerous cellular functions, in particular mitochondrial functions, which are essential for energy supply and optimal cellular functioning. Mitochondria thus appear as the primary targets of ROS since optimal cellular functioning is crucial for providing the energy for a cell to repair itself.

Interestingly, mitochondria are the major source of reactive oxygen species (ROS) and are thus particularly targeted by oxidative damage. Consequently, mitochondrial self-production of ROS causes oxidative damage that contributes to mitochondrial dysfunction and cell death.

Various antioxidants have been tested with regard to the physiological and pathological roles of ROS. Antioxidant research has provided numerous natural and designed molecules that modulate ROS with various selectivity against the different origins of ROS, being physiological (cellular signalling) or pathological. However, although ROS have been related to numerous diseases, and antioxidants have shown promises in many preclinical experiments, nearly all clinical trials of antioxidant-based therapeutics have shown limited efficacy (Orr et al., 2013. *Free Radic. Biol. Med.* 65:1047-59).

In addition, several recent studies have also demonstrated that too much reduction of ROS in cells is deleterious and it appears that an adequate balance of ROS production is necessary for cell functioning (Goodman et al., 2004 Dec. 1. *J. Natl. Cancer Inst.* 96(23):1743-50; Bjelakovic G et al., 2007 Feb. 28. *JAMA.* 297(8):842-57). As a consequence, there is a growing interest in the selective inhibition of ROS production by mitochondria that would not affect cellular signaling by cytosolic ROS production.

As mitochondrial oxidative damage contributes to a wide range of human diseases, antioxidants designed to be accumulated by mitochondria in vivo have been developed. The most extensively studied of these mitochondria-targeting antioxidants is MitoQ, which contains an antioxidant quinone moiety covalently attached to a lipophilic triphenylphosphonium cation. MitoQ has now been used in a range of in vivo studies in rats and mice and in two phase II human trials. Conditions of high ROS production are now better characterized. It appears that ROS may be produced at multiple sites of the respiratory chain in mitochondria (Quinlan C L et al., 2013 May 23. *Redox Biol.* 1:304-12). Maximal superoxide/$H_2O_2$ production occurs under conditions of high reduction of electron transporters, mainly quinones, and high values of mitochondrial membrane potential. Paradoxically, these conditions are satisfied when mitochondrial oxidative phosphorylation is low (low muscle contraction) or under low oxygen conditions (hypoxia).

The Applicant demonstrates here that AOL (Anethole trithione) does not act as a classical unspecific antioxidant molecule but more interestingly as a direct selective inhibitor of the production of oxygen radicals (ROS) predominantly at site $I_Q$ of complex I of the mitochondrial respiratory chain, the main mitochondrial site of ROS production and the main responsible site for mitochondrial dysfunctions. In addition, the Applicant demonstrates here that AOL does not affect mitochondrial oxidative phosphorylation suggesting the absence of any adverse side effects and the possibility to treat and/or prevent diseases related to free oxygen-radicals in a long term manner AOL is therefore the first known drug authorized for human use (FDA-marketing authorization) that prevents mitochondria from producing ROS at site $I_Q$.

SUMMARY

The present invention relates to an inhibitor of production of reactive oxygen species (ROS) for treating or for use in the treatment of free oxygen-radicals related diseases.

In one embodiment, said inhibitor is anethole trithione (AOL).

In one embodiment, said inhibitor inhibits mitochondrial production of ROS.

In a preferred embodiment, said inhibitor inhibits mitochondrial production of ROS at site IQ of complex I of mitochondria.

In one embodiment, said free oxygen-radicals related diseases are selected from the group comprising: age-related macular degeneration, Parkinson's disease, Alzheimer's disease, ischemic and reperfusion injury, pulmonary arterial hypertension, scleroderma, atherosclerosis, heart failure, myocardial infarction, arthritis, pulmonary toxicity, cardiopulmonary diseases, inflammatory diseases, cancer, metastasis, cardiac toxicity of anthracyclines, heart failure regardless of origin, ischemia, heart attack, stroke, thrombosis and embolism, asthma, allergic/inflammatory conditions, bronchial asthma, rheumatoid arthritis, Inflammatory Bowel Disease, Huntington's disease, cognitive disorders, Progeria, progeroid syndromes, epileptic dementia, presenile dementia, post traumatic dementia, senile dementia, vascular dementia, HIV-1-associated dementia, post-stroke dementia, Down's syndrome, motor neuron disease, amyloidosis, amyloid associated with type 11 diabetes, Creutzfelt-Jakob disease, necrotic cell death, Gerstmann-Straussler syndrome, kuru and animal scrapie, amyloid associated with long-term hemodialysis, senile cardiac amyloid and Familial Amyloidotic Polyneuropathy, cerebropathy, neurospanchnic disorders, memory loss, aluminum intoxication, reducing the level of iron in the cells of living subjects, reducing free transition metal ion levels in mammals, patients having toxic amounts of metal in the body or in certain body compartments, multiple sclerosis, amyotrophic lateral sclerosis, cataract, diabetes, cancer, liver diseases, skin ageing, transplantation, ototoxic secondary effects of aminoglycosides, neoplasms and toxicity of anti-neoplastic or immunosuppressive agents and chemicals, innate immune responses, and, Friedreich's Ataxia.

In one embodiment, said inhibitor is for preventing or for use in the prevention of metastasis.

Definitions

In the present invention, the following terms have the following meanings:

"Treating" or "treatment" or "alleviation" refers to both therapeutic treatment and prophylactic or preventative measures; wherein the object is to prevent or slow down the targeted pathologic condition or disease. Those in need of treatment include those already with the disease as well as those prone to have the disease or those in whom the disease is to be prevented. A subject or mammal is successfully "treated" for a disease or affection or condition if, after receiving the treatment according to the present invention, the subject or mammal shows observable and/or measurable reduction in or absence of one or more of the following: reduction ROS production; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

"Therapeutically effective amount" means level or amount of agent that is aimed at, without causing significant negative or adverse side effects to the target, (1) delaying or preventing the onset of a disease, disorder, or condition related to free oxygen-radicals; (2) slowing down or stopping the progression, aggravation, or deterioration of one or more symptoms of the disease, disorder, or condition related to free oxygen-radicals; (3) bringing about ameliorations of the symptoms of the disease, disorder, or condition related to free oxygen-radicals; (4) reducing the severity or incidence of the disease, disorder, or condition related to free oxygen-radicals; or (5) curing the disease, disorder, or condition related to free oxygen-radicals. A therapeutically effective amount may be administered prior to the onset of the disease, disorder, or condition related to free oxygen-radicals, for a prophylactic or preventive action. Alternatively or additionally, the therapeutically effective amount may be administered after initiation of the disease, disorder, or condition related to free oxygen-radicals, for a therapeutic action.

"Pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

"Subject" refers to an animal, including a human. In the sense of the present invention, a subject may be a patient, i.e. a person receiving medical attention, undergoing or having underwent a medical treatment, or monitored for the development of a disease. In one embodiment, the subject is a male. In another embodiment, the subject is a female.

"About": preceding a figure means plus or less 10% of the value of said figure.

DETAILED DESCRIPTION

One object of the present invention is a method for treating free oxygen-radicals related diseases in a subject in need thereof comprising the administration of an effective amount of an inhibitor of mitochondrial production of reactive oxygen species (ROS).

Another object of the present invention is an inhibitor of production of reactive oxygen species (ROS) for treating or for use in the treatment of free oxygen-radicals related diseases, wherein said inhibitor inhibits mitochondrial production of ROS.

In one embodiment, the inhibitor of the invention does not affect physiological (cytosolic) ROS production. In one embodiment, the physiological (cytosolic) ROS production is not modulated by more than 5% (increase or decrease) in presence of the inhibitor of the invention.

The term "does not affect" as used herein refers to an absence of effect of the inhibitor of the invention measured by technics known to the skilled artisan for determining the level of ROS production.

In another embodiment, the inhibitor of the invention is not an inhibitor of cytosolic ROS production.

Cytosolic ROS production is determined by the difference between total cellular ROS production and mitochondrial ROS production.

In another embodiment, the inhibitor of the invention acts upstream from ROS production.

Tests to detect cytosolic ROS production are well known in the state of the art and to the skilled artisan.

Examples of such tests include:

Measurement of global cellular ROS production: 5-(and-6)-chloromethyl-2',7'-dichlorodihydrofluorescein diacetate, acetyl ester (CM-H2DCFDA) and/or H2DCFDA are indicators for cytosolic reactive oxygen species (ROS) in cells. CM-H2DCFDA passively diffuses into cells, where its acetate groups are cleaved by intracellular esterases and its thiol-reactive chloromethyl group reacts with intracellular glutathione and other thiols. Subsequent oxidation yields a fluorescent adduct that is trapped inside the cell, thus facilitating long-term studies (Zhang, X. et al., 2008. *J. Cardiovasc. Pharmacol.* 51(5):443-449; Sarvazyan, N., 1996. *Am. J. Physiol.* 271(5 Pt 2):H2079-2085).

Measurement of mitochondrial ROS production in cells: Measuring intracellular ROS in intact cells and assigning the origin to mitochondria are far more difficult. In recent years, the proton-motive force crucial to mitochondrial function has been exploited to target a variety of compounds to the highly negative mitochondrial matrix using the lipophilic triphenylphosphonium cation TPP(+) as a "delivery" conjugate. Among these, MitoSOX Red, also called mito-hydroethidine or mito-dihydroethidium, is prevalently used for mitochondrial ROS estimation. The TPP(+) moiety of MitoSOX enables the manifold accumulation of ROS-sensitive hydroethidine in the mitochondrial matrix and the oxidation of hydroethidine by superoxide gives rise to a specific fluorescent oxidation product, 2-hydroxyethidium (Zhao, H. et al., 2005. *Proc. Natl. Acad. Sci. USA.* 102(16):5727-5732; Polster, B. M. et al., 2014. *Methods Enzymol.* 547:225-250).

In one embodiment, the inhibitor of the invention is a selective inhibitor of mitochondrial reactive oxygen species production.

The term "selective inhibitor" as used herein also refers to a compound capable of inhibiting ROS production at site IQ of complex I, while having minimal effects on ROS production from the remaining sites and on mitochondrial membrane potential ($\Delta\Psi m$) and oxidative phosphorylation. For example, on isolated mitochondria, in the presence of rotenone (i.e. when ROS production at site IQ is inhibited) and antimycin A (i.e., when ROS are produced mainly by complex III), the EC50 of the compound on the inhibition of ROS production is about 5, 6, 7, 8, 9, 10, 15, 20 times higher than in the absence of rotenone.

In one embodiment, the term "selective inhibitor" as used herein refers to a compound capable of inhibiting mitochondrial ROS production at site IQ of complex I with an $EC_{50}$ of about 10 µM. In another embodiment, said compound does not significantly inhibit cytosolic ROS production in an in vitro assay of NAD(P)H oxidase ROS production.

In another embodiment, the inhibitor or selective inhibitor of the invention is a selective inhibitor of ROS production at site $I_Q$ of complex I of the mitochondrial respiratory chain.

The term "selective inhibitor" as used herein also refers to a compound capable of inhibiting ROS production at site $I_Q$ of complex I, while having minimal effects on ROS production from the remaining sites and on mitochondrial membrane potential (ΔΨm) and oxidative phosphorylation. For example, on isolated mitochondria, in the presence of rotenone (i.e. when ROS production at site $I_Q$ is inhibited), the $EC_{50}$ of the compound on the inhibition of ROS production is about 5, 6, 7, 8, 9, 10, 15, 20 times higher than in the presence of antimycin A (i.e., when ROS are produced mainly by complex III).

Inhibition of complex I activity by rotenone and the neurotoxin MPP+ has been linked to parkinsonism in both rodents and humans suggesting a link between dysfunctional complex I, ROS production, and neurodegeneration. Compounds that are capable of inhibiting ROS production from complex I may therefore be useful in therapy.

Tests to detect specifically ROS produced at site $I_Q$ of complex I of the mitochondrial respiratory chain on isolated mitochondria from various tissues are well known to the skilled artisan.

High-throughput assays for the identification of inhibitors of ROS production at defined sites in isolated mitochondria without also altering energy production are also described. The assays identify site specific modulators of ROS production while also revealing less specific effectors like broad-acting antioxidants and various inhibitors of mitochondrial bioenergetics. Accordingly, inhibitors that discriminate between unwanted electron leak onto oxygen (ROS production) at specific sites within the electron transport chain without altering the normal energy-coupled electron and proton fluxes across the inner mitochondrial membrane may be identified. Assays adapt standard fluorescence based assays of mitochondrial ROS production using the dye Amplex UltraRed (Invitrogen) and ΔΨm using the potentiometric dye TMRM (Invitrogen) to a high throughput microplate format. A core set of five ROS and one ΔΨm assays for robust detection of functional modulation in freshly isolated skeletal muscle mitochondria are provided. Five major sites of ROS production (site $I_Q$, $I_F$, $III_{QO}$, SDH, and mGPDH) may be targeted separately by varying the substrates and inhibitors added to a common assay mixture. A counterscreen to monitor ΔΨm may be run in parallel to eliminate compounds that are likely general inhibitors or uncouplers of normal mitochondrial energy production.

In another embodiment, inhibitors are tested at 2.5 µM in duplicate against all assays. Endpoint fluorescence is normalized to DMSO and known mitochondrial inhibitor control wells included on each plate. Positive hits in each ROS assay may be initially filtered by applying a threshold of preferably 15% or more preferably 18% or even more preferably 20% or more reduction in that assay. Each ROS assay may be employed as a counterscreen against the others while also eliminating compounds that altered ΔΨm in the TMRM-based counterscreen. Therefore, filtered hits may be subsequently assessed to eliminate those that altered the other ROS assays by more than e.g., 20% or 18% or 15% or ΔΨm by more than, preferably 10% or more preferably 5% or even more preferably 4%.

In another embodiment, inhibitors that are selective inhibitors of ROS production from a single site of ROS production decrease ROS production from one of the ROS production site $I_Q$, $I_F$, $III_{QO}$, SDH, and mGPDH by greater than 18%, while affecting ROS production from the remaining sites of ROS production by less than 10%.

Complex I of the respiratory chain can generate ROS from two distinct sites: the ubiquinone binding site and the flavin mononucleotide site.

Ubiquinone Binding Site of Complex I ($I_Q$):

To specifically analyze ROS production from $I_Q$, 5 mM succinate may be used as the substrate to supply electrons to the respiratory chain. $I_Q$ ROS production is exceptionally sensitive to changes in the proton motive force (PMF) across the mitochondrial inner membrane (PMF=ΔΨm+ΔpH). Therefore, a conservative threshold for the ΔΨm assay when evaluating selectivity of hits in the $I_Q$ ROS assay may be utilized.

Electron leak from site $I_Q$ is best characterized during reverse transport from a reduced Q-pool to matrix $NAD^+$ via CI in the presence of a strong PMF. Experimentally, conditions that favor $I_Q$ ROS production are considered far removed from physiology leading many to dismiss its relevance despite its capacity for high rates. However, even when provided with lower concentrations of both glutamate (to feed electrons forward through CI) and succinate (to feed electrons in reverse), respiring mitochondria still produce significant levels of rotenone-sensitive ROS (i.e. $I_Q$ ROS). Further, comparative analyses show an inverse relationship between maximal ROS production from site $I_Q$ (but not site $I_F$) and maximum life span across diverse vertebrate species (Lambert, A. et al., 2007. *Aging Cell.* 6(5):607-18; Lambert, A. et al., 2010. *Aging Cell.* 9(1):78-91.). Therefore, selective modulators of $I_Q$ ROS would offer unique opportunities to probe the putative role of mitochondrial ROS production in normal and pathological processes.

Flavin Binding Site of Complex I ($I_F$):

To specifically analyze ROS production from $I_F$, the substrate solution to supply electrons to the respiratory chain may comprise 5 mM glutamate, 5 mM malate and 4 µM rotenone. Site $I_F$ produces ROS at a rate proportional to the reduction state of the NADH pool in the mitochondrial matrix (Treberg, J. et al., 2011. *J. Biol. Chem.* 286(36): 31361-72). Blockade of site $I_Q$ with the pesticide rotenone can increase ROS production from site $I_F$ by preventing oxidation of the flavin. Maximal ROS production from the flavin binding site of complex I (site $I_F$) is relatively low compared to sites $I_Q$ and $III_{QO}$ and this may lead to higher variability in this assay and subsequently a higher false positive rate of hit calling in the original screen.

In another embodiment, the inhibitor of the invention does not affect significantly oxidative phosphorylation directly on mitochondria, preferably oxidative phosphorylation is modulated by less than 10, 9, 8, 7, 6, 5%.

Diseases related to free oxygen-radicals relate to oxidative stress imbalances and mitochondrial dysfunction. In particular, diseases related to mitochondrial dysfunctions are induced by mitochondrial ROS production.

Diseases related to free oxygen-radicals include but are not limited to: aging diseases, auto-immune diseases, cardiovascular diseases, progeroid syndromes, Parkinsonian syndromes, neurological diseases, ischemic and reperfusion injuries, infectious diseases, muscles diseases, lung, kidney and liver diseases.

Aging diseases include but are not limited to: age-related macular degeneration (AMD), skin ageing, UV damage to the skin, thinning, sagging, wrinkling, the appearance of age spots, broken blood vessels and areas of dryness, seborrhoeic keratosis, solar keratoses, Kindler Syndrome, Bowen's disease, skin cancer, arthritis, ankylosing spondylitis, inflammatory polyarthropathies, knee arthritis, epidemic polyarthritis, psoriatic arthritis, cataract, deafness, cancer, metastasis, metastasis processes prevention, liver diseases, transplantation, neoplasms and toxicity of anti-neoplastic or immunosuppressive agents and chemicals, osteoporosis, poikiloderma, acrogeria, hereditary sclerosing poikiloderma, dyskeratosis congenita, xeroderma pigmentosum, Bloom's syndrome, Fanconi anemia, Cockayne syndrome, and pollution-induced diseases.

Autoimmune diseases include but are not limited to: multiple sclerosis, rheumatoid arthritis, systemic lupus erythematosis, type I diabetes mellitus, Crohn's disease; myasthenia gravis, Grave's disease, scleroderma, Sjogren's syndrome, ulcerative colitis, primary biliary cirrhosis, autoimmune hepatitis, Hashimoto's thyroiditis, ankylosing spondylitis, psoriasis. The autoimmune disease can be an autoimmune disease related to blood disorders such as autoimmune hemolytic anemia, pernicious anemia and autoimmune thrombocytopenia. The autoimmune disease can also be temporal areritis, anti-phospholipid syndrome, vasculitides such as Wegener's granulomatosis and Behcet's disease. Other autoimmune diseases include polymyositis, drmatomyositis, spondyloarthropthies such as ankylosing spondylitis, anti-phospholipid syndrome, and polymyocysitis.

Cardiovascular diseases include but are not limited to: hypertension, cardiac toxicity of anti-cancer drugs, cardiac toxicity of anthracyclines, cardiac toxicity of quinolones, heart failure regardless of origin, ischemia, heart attack, stroke, atherosclerosis, cardiac fibrillation, hypertension, thrombosis and embolism, allergic/inflammatory conditions such as bronchial asthma, rheumatoid arthritis, inflammatory Bowel disease, type II diabetes, diabetes mellitus and deafness (DAD) or Ballinger-Wallace syndrome, inflammatory diseases, rheumatic fever, pulmonary arterial hypertension, innate immune responses, cardiopulmonary diseases such as: chronic obstructive pulmonary disease, pulmonary embolism, pericarditis, coarctation of aorta, tetralogy of Fallot, aortic stenosis, mitral stenosis, aortic regurgitation, mitral regurgitation, pneumoconiosis, bronchiectasis, cardiomyopathies, endothelial nitroglycerin tolerance.

Progeroid syndromes include but are not limited to: progeria, Bloom syndrome, Cockayne syndrome, De Barsy syndrome, dyskeratosis congenita, restrictive dermopathy, Rothmund-Thomson syndrome, trichothiodystrophy, Werner syndrome, Wiedemann-Rautenstrauch syndrome, xeroderma pigmentosum.

Parkinsonian syndromes include but are not limited to: Parkinson's disease (PD), progressive supranuclear palsy, multiple system atrophy, corticobasal degeneration or Lewy body dementia, toxin-induced Parkinsonism, and an early-onset variant of PD such as an autosomal recessive PARK6-linked Parkinsonism or an autosomal recessive PINK1-linked Parkinsonism.

Neurologic diseases include but are not limited to: dementia, Alzheimer's disease, Parkinson's disease and ageing, Huntington's disease, Friedreich's Ataxia, Wilson's disease, Leigh syndrome, Kearns-Sayre syndrome, Leber hereditary optic neuropathy, cognitive disorders, mood disorders, movement disorders, tardive dyskinesia, brain injury, apoptosis, dementia, epilepsy, epileptic dementia, presenile dementia, post traumatic dementia, senile dementia, vascular dementia, HIV-1-associated dementia, post-stroke dementia, schizophrenia, Down's syndrome, motor neuron disease, amyloidosis, amyloid associated with type II diabetes, Creutzfelt-Jakob disease, necrotic cell death, Gerstmann-Straussler syndrome, kuru and animal scrapie, amyloid associated with long-term hemodialysis, senile cardiac amyloid and familial amyloidotic polyneuropathy, cerebropathy, neurospanchnic disorders, memory loss, aluminum intoxication, reducing the level of iron in the cells of living subjects, reducing free transition metal ion levels in mammals, patients having toxic amounts of metal in the body or in certain body compartments, multiple sclerosis, amyotrophic lateral sclerosis, akinetopsia, alcohol-related dementia, primary age-related tauopathy, anomic aphasia, anosognosia, apraxia, apraxia of speech, auditory verbal agnosia, frontotemporal dementia, frontotemporal lobar degeneration, logopenic progressive aphasia, neurofibrillary tangle, phonagnosia, Pick's disease, primary progressive aphasia, progressive nonfluent aphasia, semantic dementia, steroid dementia syndrome, visuospatial dysgnosia, ototoxic secondary effects of aminoglycosides, cocaine toxicity.

Ischemic and reperfusion injury include but are not limited to: stroke, brain ischemia, brainstem stroke syndrome, carotid endarterectomy, cerebellar stroke syndrome, cerebral achromatopsia, cerebral hemorrhage, cerebral infarction, cerebral venous sinus thrombosis, intraparenchymal hemorrhage, intracranial hemorrhage, lacunar stroke, lateral medullary syndrome, lateral pontine syndrome, partial anterior circulation infarct, posterior circulation infarct, silent stroke, troke Association, stroke belt, stroke recovery, transient ischemic attack, Watershed stroke, Weber's syndrome, obesity, organ preservation for transplantation, ischemia, reperfusion injury.

Infectious diseases include but are not limited to: hepatitis C, sepsis, infectious myopathies, septic shock.

Muscles diseases include but are not limited to: myopathies, mitochondrial myopathies, facioscapulohumeral muscular dystrophy, facioscapulohumeral muscular dystrophy type 1, facioscapulohumeral muscular dystrophy type 2, Ryanodine Receptor 1 (RYR1) related myopathy, selenoprotein 1 (SEPN1)-related myopathy Kearns-Sayre syndrome, cardiomyopathies, movement disorder, immobilization-induced muscle atrophy, skeletal muscle burn injury, Dupuytren's contracture.

Lung, kidney and liver diseases include but are not limited to: cystic fibrosis, asthma, pollution-induced diseases, cardio-pulmonary diseases, pulmonary arterial hypertension, chronic obstructive pulmonary disease, pulmonary embolism, pneumoconiosis, bronchiectasis, bronchial asthma, ventilator-induced diaphragm dysfunction, lung cancer, alcohol fatty liver disease, fatty liver disease, diabetes, kidney preservation ex vivo, liver inflammation in hepatitis C, kidney damage in type I diabetes, cirrhosis.

Diseases to be treated in particular in the present invention are aging disease, AMD, skin aging, cardiovascular diseases such as for example cardiac toxicity of anthracyclines, progeria and progeroid syndromes, Parkinson's disease, Alzheimer's disease, Friedreich's Ataxia, ischemia reperfusion, cardio-pulmonary diseases, asthma, cancer, metastasis, pollution-induced diseases.

In one embodiment, a disease to be particularly prevented in the present invention is metastasis. Indeed, ROS production is involved in mechanisms of tumor growth and metastasis: tumor cell migration, invasion, clonogenicity, metastatic take, and spontaneous metastasis are promoted by the natural selection of a mitochondrial phenotype associated with ROS production and aberrant TCA cycle activity, a mechanism named "metastatic mitochondrial switch" (Porporato et al., 2014. *Cell Reports*. 8:754-766). ROS hyper production also promotes angiogenesis and reciprocally inhibitors of ROS production are antiangiogenic products.

In one embodiment, the inhibitor or selective inhibitor of the invention is of one of the following formulas:

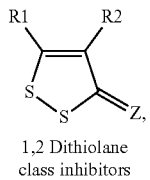
1,2 Dithiolane class inhibitors

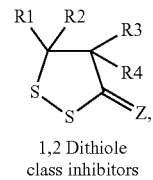
1,2 Dithiole class inhibitors

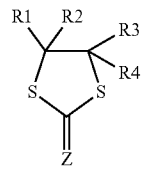
1,3 Dithiole class inhibitors

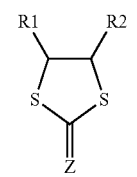
1,3 Dithiolane class inhibitors and oxides, derivatives and metabolites thereof, wherein
Z is S, O, NR, $R_2$ or $CR_2$;
R is —H, —OH, $C_1$-$C_5$ alkyl, $C_1$-$C_5$ alkoxy or $C_1$-$C_5$ alkoxycarbonyl;
R2, together with the atoms to which it is bonded, comprises a spiro ring;
R1, R2, R3, and R4 independently are —H, -alkyl, -aryl, -alkylaryl, a heterocycle, a halogen, -alkoxycarbonyl ($C_1$-$C_5$) or -carboxyl;
wherein either alkyl is a $C_1$-$C_{10}$ linear or branched chain, saturated or unsaturated moiety, which is optionally substituted by 1, 2 or more independently selected ether (—O—), halogen, alkyl ($C_1$-$C_5$), —OH, alkoxy ($C_1$-$C_5$), alkoxycarbonyl, ($C_1$-$C_5$), carboxyl, amido, alkyl amido ($C_1$-$C_5$), amino, mono- or dialkylamino ($C_1$-$C_5$), alkyl carbamoyl (C1-C5), thiol, alkylthio ($C_1$-$C_5$), or benzenoid aryl; and
wherein the -aryl and -alkylaryl substituent for R1, R2, R3 and R4 comprises a benzenoid group ($C_6$-$C_{14}$), wherein the benzenoid group is optionally substituted with 1, 2 or more independently selected —$SO_3H$, halogen, alkyl ($C_1$-$C_5$), —OH, alkoxy ($C_1$-$C_5$), alkoxycarbonyl, ($C_1$-$C_5$), carboxyl, amido, alkyl amido ($C_1$-$C_5$), amino, mono- or dialkylamino ($C_1$-$C_5$), alkyl carbamoyl ($C_1$-$C_5$), thiol, alkylthio ($C_1$-$C_5$); and
wherein the heterocycle is defined as any 4, 5 or 6 membered, optionally substituted heterocyclic ring, saturated or unsaturated, containing 1-3 ring atoms selected from N, O and S, the remaining ring atoms being carbon; and wherein said substituents on said aryl or said heterocyclic are selected from the group consisting of halogen, alkyl ($C_1$-$C_5$), hydroxyl, alkoxy ($C_1$-$C_5$), alkoxycarbonyl ($C_1$-$C_5$), carboxyl, amido, alkyl amido ($C_1$-$C_5$), amino, mono and dialkyl amino ($C_1$-$C_5$), alkyl carbamoyl ($C_1$-$C_5$), thiol, alkylthio ($C_1$-$C_5$), benzenoid, aryl, cyano, nitro, haloalkyl ($C_1$-$C_5$), alklsulfonyl ($C_1$-$C_5$), or sulfonate, or
one of R1 and R2 and one of R3 and R4 together with the carbon atoms to which they are attached comprise a fused bicyclic or tricyclic compound, which is saturated or unsaturated, heterocyclic or carbocyclic and wherein the rings are all optionally substituted 5-, 6-, 7- or 8-membered rings, with substituents optionally selected from alkyl, alkoxy, —$SO_3H$, —OH and halogen, or
R1 and R2 together or R3 and R4 together independently are oxime (=NOH).

Examples of 1,2 dithiolane class inhibitors include but are not limited to: lipoamide (1,2 dithiolane); 1,2-Dithiolane-4-carboxylic acid; 4-octyl-1,3-dithiolane-2-thione; 4-decyl-1,3-dithiolane-2-thione; 4-dodecyl-1,3-dithiolane-2-thione; 4-tetradecyl-1,3-dithiolane-2-thione; and a 1,3-dithiolane-2-thione.

Examples of 1,2 dithiole class inhibitors include but are not limited to: 4-methyl-5-(2-pyrazinyl)-3-dithiolethione (oltipraz); 5-(4-methoxyphenyl)-3H-1,2-dithiole-3-thione (anetholetrithione or AOL), anethole dithiolethione (ADT), ADO, 1,2-dithiole-3-thione; 5-(4-phenyl-1,3-butadienyl)-1,2-dithiol-3-thione, 5-4 (4-chlorophenyl)-1,3-butadienyl-1,2-dithiol-3-thione, 5-{4-(4-methoxyphenyl)-1,3-butadienyl}-1,2-dithiol-3-thione, 5-{4-(p-toluyl)-1,3-butadienyl}-1,2-dithiol-3-thione, 5-{4-(o-chlorophenyl)-1,3-butadienyl}-1,2-dithiol-3-thione and 5-{4-(m-methyl phenyl)-1,3-butadienyl}-1,2-dithiol-3-thione.

Examples of 1,3 dithiole class inhibitors include but are not limited to: diisopropyl 1,3-dithiol-2-ylidenemalonate (malotilate); 1,3-dithiolo(4.5-d)-1,3-dithiino-2-thione; 1,3-dithiolo(4.5-d)-1,3-dithiole-2-thione; 5-chloro-1,3-dithiolo (4.5-d)-1,3-dithiole-2-thione; and 5-cyano-1,3-dithiolo(4.5-d)-1,3-dithiole-2-thione.

Examples of 1,3 dithiolane class inhibitors include but are not limited to: 5-(1-carbonyl-L-amino-acid)-2,2-dimethyl-[1,3]dithiolane-4-carboxylic acid; Hexahydro-1-3-benzodithiole-2-thione; 4-Octyl-1,3-dithiolane-2-thione; 4-Decyl-1,3-dithiolane-2-thione; 4-Dodecyl-1,3-dithiolane-2-thione.

The inhibitor or selective inhibitor of the invention is preferably selected from the group comprising: 5-(4-methoxyphenyl)-3H-1,2-dithiole-3-thione (anetholetrithione or AOL), anethole dithiolethione (ADT), ADO, 1,2-dithiole-3-thione, 1,2-dithiolane, 1,3-dithiole-2-thione, 4-methyl-5-(2-pyrazinyl)-3-dithiolethione (oltipraz), and diisopropyl 1,3-dithiol-2-ylidenemalonate (malotilate) or derivatives or analog thereof.

Examples of inhibitors or selective inhibitors of the invention include but are not limited to:

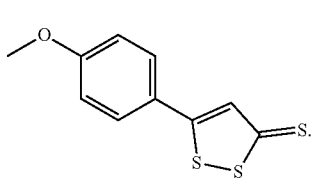
5-(4-methoxyphenyl)-3H-1,2-dithiole-3-thione (AOL)

Oltipraz

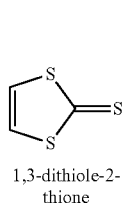
1,3-dithiole-2-thione

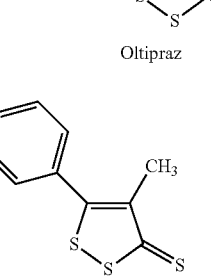
ADT

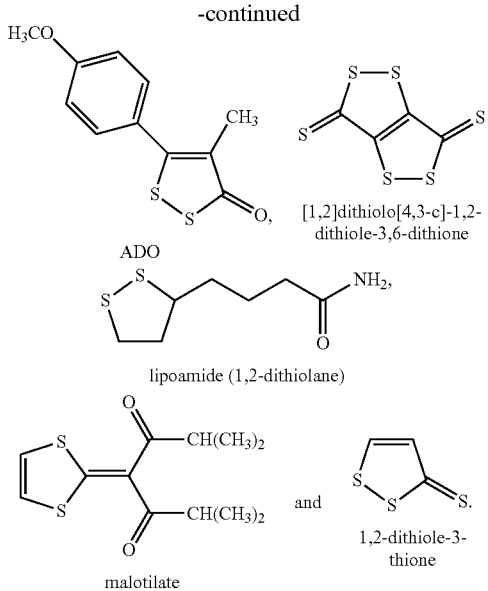

In one embodiment, the inhibitor of the invention is:

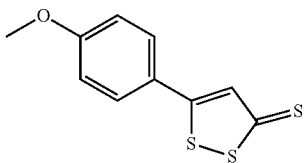

5-(4-methoxyphenyl)-3H-1,2-dithiole-3-thione (AOL).

5-(4-methoxyphenyl)-3H-1,2-dithiole-3-thione (AOL).

In one embodiment, the inhibitor of the invention is not a chelating agent, preferably, a chelating agent of Fe and/or Cu.

In one embodiment, the inhibitor of the invention is not oltipraz.

In one embodiment, the inhibitors or selective inhibitors are selected from those described in the following Patent Application: US2004/053989.

In another embodiment, the inhibitors or selective inhibitors are selected from those described in the following Patents: U.S. Pat. No. 3,040,057; EP0576619; U.S. Pat. Nos. 3,576,821; 3,959,313; 3,109,772.

In one embodiment, the inhibitor is not N-cyclohexyl-4-(4-nitrophenoxy)benzenesulfonamide.

The present invention also relates to a composition for treating diseases related to free oxygen-radicals in a subject in need thereof, comprising or consisting of or consisting essentially of the inhibitor as hereinabove described.

The present invention also relates to a composition for treating or for use in treating free oxygen-radicals related diseases, wherein said composition comprises or consists of or consists essentially of an inhibitor or selective inhibitor of mitochondrial production of ROS.

The present invention also relates to a pharmaceutical composition for treating diseases related to free oxygen-radicals in a subject in need thereof, comprising or consisting of or consisting essentially of the inhibitor as hereinabove described in combination with at least one pharmaceutically acceptable excipient.

The present invention also relates to a pharmaceutical composition for treating or for use in treating free oxygen-radicals related diseases, wherein said pharmaceutical composition comprises or consists of or consists essentially of an inhibitor or selective inhibitor of mitochondrial production of ROS and at least one pharmaceutically acceptable excipient.

The present invention also relates to a medicament for treating diseases related to free oxygen-radicals in a subject in need thereof, comprising or consisting of or consisting essentially of the inhibitor as hereinabove described.

The present invention also relates to a medicament for treating or for use in treating free oxygen-radicals related diseases, wherein said medicament comprises or consists of or consists essentially of an inhibitor or selective inhibitor of mitochondrial production of ROS.

Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, such as, for example, BHA, BHT, citric acid, ascorbic acid, tetracycline, and the like.

Other examples of pharmaceutically acceptable excipients that may be used in the composition of the invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In addition some excipients may include, surfactants (e.g. hydroxypropylcellulose); suitable carriers, such as, for example, solvents and dispersion media containing, for example, water, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose; and the like.

In one embodiment, the composition, the pharmaceutical composition or the medicament of the invention is to be administered systemically or locally.

In one embodiment, the composition, the pharmaceutical composition or the medicament of the invention is to be administered orally, by injection, topically, nasally, buccally, rectally, vaginally, intratracheally, by endoscopy, transmucosally, and by percutaneous administration.

In one embodiment, the composition, the pharmaceutical composition or the medicament of the invention is injected, preferably systemically injected. Examples of formulations adapted to systemic injections include, but are not limited to: liquid solutions or suspensions, solid forms suitable for solution in, or suspension in, liquid prior to injection. Examples of systemic injections include, but are not limited to, intravenous, subcutaneous, intramuscular, intradermal and intraperitoneal injection, and perfusion. In another embodiment, when injected, the composition, the pharmaceutical composition or the medicament of the invention is sterile. Methods for obtaining a sterile pharmaceutical composition include, but are not limited to, GMP synthesis (GMP stands for "Good manufacturing practice").

In another embodiment, the composition, the pharmaceutical composition or the medicament of the invention is orally administered. Examples of formulations adapted to oral administration include, but are not limited to: solid forms, liquid forms and gels. Examples of solid forms adapted to oral administration include, but are not limited to, pill, tablet, capsule, soft gelatine capsule, hard gelatine capsule, caplet, compressed tablet, cachet, wafer, sugar-coated pill, sugar coated tablet, or dispersing/or disintegrating tablet, powder, solid forms suitable for solution in, or suspension in, liquid prior to oral administration and effervescent tablet. Examples of liquid form adapted to oral administration include, but are not limited to, solutions, suspensions, drinkable solutions, elixirs, sealed phial, potion, drench, syrup and liquor.

In another embodiment, the composition, the pharmaceutical composition or the medicament of the invention is topically administered. Examples of formulations adapted to topical administration include, but are not limited to, sticks, lipsticks, waxes, creams, lotions, ointments, balms, gels, glosses, sunscreen preparations, cosmetics, masks, leave-on washes or cleansers, depilatory preparations and/or the like.

Topical administration characterizes the delivery, administration or application of the composition, the pharmaceutical composition or the medicament of the invention directly to the site of interest for a localized effect (generally onto one or more exposed or outer surfaces thereof, such as the outermost layer of the epidermis, which is exposed and visually observable), for example, using hands, fingers or a wide variety of applicators (roll-up, roll-on or other stick container, tube container, cotton ball, powder puff, Q-tip, pump, brush, mat, cloth and/or the like). The application may be made, for example, by laying, placing, rubbing, sweeping, pouring, spreading and/or massaging into, or onto, the skin, or by any other convenient or suitable method. Preferably, topical administration is effected without any significant absorption of components of the composition into the subject's blood stream (to avoid a systemic effect).

The composition, the pharmaceutical composition or the medicament of the invention of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g. gauze, can be impregnated with the compositions in solution, lotion, cream, ointment or other such form can also be used for topical application.

One object of the present invention is a cosmetic composition comprising the inhibitor of the invention.

Another object of the invention is a cosmeceutical composition comprising the inhibitor of the invention.

In another embodiment, the composition of the invention can also be applied topically using a transdermal system, such as one of an acrylic-based polymer adhesive with a resinous crosslinking agent impregnated with the composition and laminated to an impermeable backing.

In one embodiment, the composition of the present invention can be administered as a transdermal patch, more particularly as a sustained-release transdermal patch. The transdermal patches can include any conventional form such as, for example, adhesive matrix, polymeric matrix, reservoir patch, matrix or monolithic-type laminated structure, and are generally comprised of one or more backing layers, adhesives, penetration enhancers, an optional rate controlling membrane and a release liner which is removed to expose the adhesives prior to application. Polymeric matrix patches also comprise a polymeric-matrix forming material. Suitable transdermal patches are described in more detail in, for example, U.S. Pat. Nos. 5,262,165; 5,948,433; 6,010,715 and 6,071,531, the disclosure of each of which are incorporated herein in their entirety.

Examples of formulations adapted to transdermal administration include, but are not limited to, ointment, paste, cream, film, balm, patch, such as, for example, transdermal patch, gel, liposomal forms and the like.

In one embodiment, the transdermal composition is an ointment, paste, cream; film, balm, patch, such as, for example, transdermal patch, gel, liposomal forms or the like.

In one embodiment of the invention, the ointment is an oleaginous ointment; an emulsified ointment such as, for example, oil-in-water or a water-in-oil ointment; or a water-soluble ointment, preferably is an oleaginous ointment.

In one embodiment of the invention, the oleaginous ointment uses bases such as, for example, plant and animal oils; plant and animal fats; waxes; vaseline, such as, for example, white vaseline or vaseline oil; and paraffin such as, for example, liquid paraffin or paraffin oil.

In one embodiment of the invention, the transdermal composition further comprises one or more excipients. Suitable pharmaceutically acceptable excipients are well known from the skilled person. Examples of suitable excipients include, but are not limited to, carriers, emulsifying agents, stiffening agents, rheology modifiers or thickeners, surfactants, emollients, preservatives, humectants, buffering agents, solvents, moisturizing agents and stabilizers.

In another embodiment, a particular administration route may be intraocularly. In another embodiment, the administration route may be a topical ocular administration, such as, for example, the administration of eye drops or by bathing the eye in an ophthalmic solution comprising the inhibitor of the invention.

The ophthalmic solution refers to sterile liquid, semi-solid or solid preparations intended for administration upon the eyeball and/or to the conjunctiva, or for insertion in the conjunctival sac or for administration into the posterior segment of the eye. As used herein, the term "posterior segment of the eye" refers to the back two third of the eye, comprising the anterior hyaloids membrane and the structures behind it (vitreous humor, retina, choroid, optic nerve). In particular, an ophthalmic composition may be administered into the vitreous, for example by intravitreous injection. Examples of ophthalmic compositions include, but are not limited to, eye drops, eye lotions, powders for eye drops and powders for eye lotions, and compositions to be injected into the conjunctival sac or into the vitreous.

Examples of carriers include, but are not limited to, water; buffered saline; petroleum jelly (Vaseline, also known as white soft paraffin); petrolatum; oils, such as, for example, mineral oil, vegetable oil, animal oil, paraffin oil, castor oil or vaseline oil; organic and inorganic waxes, such as, for example, microcrystalline, paraffin, bees wax and ozocerite wax; natural polymers, such as, for example, xanthanes, gelatin, cellulose, collagen, starch, or gum arabic; synthetic polymers; alcohols; polyols; and the like. In one embodiment of the invention, the carrier is a base cream, comprising an emulsifying agent, an oil-phase ingredient and a water phase ingredient.

Examples of well-known ointment or lotion base excipients include, but are not limited to, Vaseline, Plastibase™ (which is a base prepared with polyethylene (average molecular weight of about 21000 Da) and liquid paraffin) or ESMA-P™ (made of microcrystalline wax).

Examples of emulsifying agents include, but are not limited to, cetyl alcohol; cetostearyl alcohol; stearyl alcohol; carboxypolymethylene; polycarbophil; polyethylene glycol and derivatives thereof; polyoxyethylene and derivatives thereof, such as, for example, polysorbate 20 or polysorbate 80, alone or in combination with fatty alcohols such as, for example, cetyl alcohol, stearyl alcohol and cetostearyl alcohol; and sorbitan esters, such as, for example, sorbitan fatty acid ester.

Examples of oil-phase ingredient include, but are not limited to, Vaseline, such as, for example, white Vaseline, yellow Vaseline or Vaseline oil; paraffin such as, for example, liquid paraffin or paraffin oil; dimethicone and mixtures thereof.

Examples of water-phase ingredients include, but are not limited to, water, glycerol and propyleneglycol.

Examples of stiffening agents include, but are not limited to, stearyl alcohol, cetostearyl alcohol, and cetyl alcohol.

Examples of rheology modifiers or thickeners include, but are not limited to, carbomers such as, for example, Carbopol®, and polyoxyethylene tallow amines such as, for example, Ethomeen®.

Examples of surfactants include, but are not limited to, anionic, cationic, amphoteric, and nonionic surfactants, such as, for example, sodium lauryl sulfate, cetostearyl alcohol, cetyl alcohol, magnesium lauryl sulfate, a wax, or a combination thereof.

Examples of emollients include, but are not limited to, white or yellow petrolatum (white or yellow vaseline), liquid petrolatum (liquid vaseline), paraffin, or aquaphor.

Examples of preservatives include, but are not limited to, antimicrobial preservatives such as, for example, nipagin (methyl hydroxybenzoate), nipasol (hydroxybenzoate), butylparaben, ethylparaben, methylparaben, propyl paraben potassium, propyl paraben sodium; parahydroxybenzoate esters; sorbic acid; potassium sorbate; benzoic acid; parabens; chlorbutanol; phenol; thimerosal; sodium benzoate and benzyl alcohol.

Examples of humectants include, but are not limited to, propylene glycol and propylene glycol alginate.

Examples of buffering agents include, but are not limited to, sodium hydroxide, citric acid and potassium hydroxide.

Examples of solvents include, but are not limited to, water, isopropanol, benzyl alcohol, and propylene glycol.

Examples of moisturizing agents include, but are not limited to, glycerin, mineral oil, polyoxyethylene hardened castor oil and Vaseline, propylene glycol; paraffins; waxes, such as, for example, bees wax; polyethylene glycols or mixtures thereof, such as, for example, macrogol (macrogol is a mixture of polyethylene glycols of different molecular weights); stearyl alcohol; benzyl alcohol; parahydrobenzoate esters (parabens); gelled hydrocarbon; citric acid; squalene; lanolins; glycerin; polyoxyethylene hardened castor oil; sorbitan fatty ester; glycerin fatty ester; animal and vegetable fats; oils; starch; tragacanth; cellulose derivatives; silicones; bentonites; silicic acid; talc; zinc oxide and mixtures thereof.

Examples of stabilizers include, but are not limited to, carbohydrates such as, for example, sucrose, lactose and trehalose; sugar alcohols such as, for example, mannitol and sorbitol; amino acids such as, for example, histidine, glycine, phenylalanine and arginine.

In one embodiment of the invention, the composition, pharmaceutical composition or medicament of the invention may be used in conjunction with delivery systems that facilitate delivery of the agents to the central nervous system. For example, various blood brain barrier (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable barrier to delivery of pharmacological agents to the CNS for treatment of disorders or maintaining or enhancing normal and desirable brain functions, such as cognition, learning, and memory.

In one embodiment, the inhibitor, the composition, the pharmaceutical composition or the medicament is administered in a sustained-release form. In another embodiment, the composition, the pharmaceutical composition or the medicament comprises a delivery system that controls the release of the modulator.

In one embodiment, the inhibitor, the composition, the pharmaceutical composition or the medicament of the invention is administered at a dose determined by the skilled artisan and personally adapted to each subject.

It will be understood that the total daily usage of the inhibitor, the composition, pharmaceutical composition and medicament of the present invention will be decided by the attending physician within the scope of sound medical judgment. The specific therapeutically effective amount for any particular patient will depend upon a variety of factors including the disease being treated and the severity of the disease; the specific composition employed, the age, body weight, general health, sex and diet of the subject; the time of administration, route of administration, the duration of the treatment; drugs used in combination or coincidental with the polypeptide or nucleic acid sequence employed; and like factors well known in the medical arts. For example, it is well within the skill of the art to start doses of a therapeutic compound at levels lower than those required to achieve the desired therapeutic effect and to gradually increase the dosage until the desired effect is achieved; but, at the opposite, it can be equally useful to start with a loading dose, a manner to reach steady-state plasma concentration more quickly, and then to follow with a maintenance dose calculated to exactly compensate the effect of the elimination process.

In one embodiment, a therapeutically effective amount of the inhibitor, the composition, the pharmaceutical composition or the medicament of the invention is administered at least once a day, twice a day, at least three times a day.

In another embodiment, a therapeutically effective amount of the inhibitor, the composition, the pharmaceutical composition or the medicament of the invention is administered every two, three, four, five, six days.

In another embodiment, a therapeutically effective amount of the inhibitor, the composition, the pharmaceutical composition or the medicament of the invention is administered twice a week, every week, every two weeks, once a month.

In one embodiment of the invention, the daily amount of the inhibitor, the composition to be administered to a subject ranges from about 2 mg/day to about 2000 mg/day, from about 2 mg/day to about 1500 mg/day, from about 2 mg/day to about 1000 mg/day, from about 2 mg/day to about 500 mg/day, from about 2 mg/day to about 200 mg/day, from about 5 mg/day to about 2000 mg/day, from about 5 mg/day to about 1500 mg/day, from about 5 mg/day to about 1000 mg/day, from about 5 mg/day to about 500 mg/day, from about 5 mg/day to about 200 mg/day, from about 10 mg/day to about 2000 mg/day, from about 10 mg/day to about 1500 mg/day, from about 10 mg/day to about 1000 mg/day, from about 10 mg/day to about 500 mg/day, from about 10 mg/day to about 200 mg/day.

In one embodiment of the invention, the daily amount of the inhibitor, the composition to be administered to a subject ranges from about 1 mg/kg/day to about 20 mg/kg/day, from about 1 mg/kg/day to about 15 mg/kg/day, from about 1 mg/kg/day to about 12 mg/kg/day, from about 1 mg/kg/day to about 10 mg/kg/day, from about 1 mg/kg/day to about 9 mg/kg/day, from about 1 mg/kg/day to about 8 mg/kg/day, from about 1 mg/kg/day to about 7 mg/kg/day.

In another embodiment, the inhibitor, the composition of the invention is to be administered at a quantity of about 5 mg to about 2000 mg, from about 5 mg to about 1500 mg, from about 5 mg to about 1000 mg, from about 5 mg to about 500 mg, from about 5 mg to about 200 mg.

In one embodiment, the method of the invention is for a chronic treatment. In another embodiment, the method of the invention is for an acute treatment.

In one embodiment of the invention, the subject is diagnosed with a free oxygen-radicals related disease. In another embodiment of the invention, the subject is at risk of developing a free oxygen-radicals related disease.

In one embodiment, said subject is an adult, a teenager, a child, a young child or a new born child.

Another object of the invention is a conservation medium comprising the inhibitor of the invention.

In one embodiment, the conservation medium is for the preservation of organs. In one embodiment, said organs include, but are not limited to: heart, liver, kidney, lung, pancreas, intestine. In one embodiment, said organs are for transplantation.

In one embodiment, the conservation medium comprises the inhibitor of the invention at a concentration ranging 5 µM to 120 µM, i.e., at a concentration of about 5 µM, 10 µM, 20 µM, 50 µM, 80 µM, 100 µM or 120 µM.

Another object of the present invention is a method for inhibiting free oxygen-radicals production in a subject in need thereof by acting on mitochondria at site $I_Q$ of complex I, comprising the administration of an effective amount into the subject of an inhibitor of reactive oxygen species.

Another object of the present invention is a method for treating aging diseases in a subject in need thereof by acting on mitochondria at site $I_Q$ of complex I, comprising the administration of an effective amount into the subject of an inhibitor of reactive oxygen species.

Another object of the present invention is a method for inhibiting free oxygen-radicals production in a subject in need thereof without inhibiting cytosolic ROS production, comprising the administration of an effective amount into the subject of an inhibitor of reactive oxygen species.

Another object of the present invention is a method for increasing insulin secretion in a subject in need thereof by acting on mitochondria at site $I_Q$ of complex I, comprising administrating an effective amount of an inhibitor of production of reactive oxygen species as described here above.

Another object of the present invention is a method for protecting neurons in a subject in need thereof by acting on mitochondria at site $I_Q$ of complex I, comprising administrating an effective amount of an inhibitor of production of reactive oxygen species as described here above.

Another object of the invention is an inhibitor of mitochondrial reactive oxygen species production for treating at least one disease related to free oxygen-radicals.

Another object of the invention is the use of an inhibitor of mitochondrial reactive oxygen species production for treating at least one disease related to free oxygen-radicals.

Another object of the invention is the use of an inhibitor of mitochondrial reactive oxygen species production for the preparation of a medicament for treating at least one disease related to free oxygen-radicals.

BRIEF DESCRIPTION OF THE DRAWINGS

FIG. 1 (A to D) illustrates the absence of effect of AOL on mitochondrial respiration.

FIG. 2 (A to E) presents the main sites of oxygen radicals' production by isolated mitochondria in the presence of substrates of both complexes I and III in the presence of ATR (state 4) in order to obtain maximal mitochondrial ROS production. As previously stated, mitochondrial ROS production is highly dependent on mitochondrial activity and conditions. Although AOL has been tested under numerous conditions, for the sake of clarity, we chose to present here only the most demonstrative results. The presence of all the substrates (i.e. Glutamate+Malate+Succinate), giving the electrons to the whole chain, is the closest to in situ conditions in the cell. Under these conditions of substrates, we evaluated the effect of the presence of AOL on ROS production by the complete chain under ATR (inhibition of phosphorylation: maximum production), and by the complex I (inhibited by rotenone) and complex II (inhibited by Antimycin A).

FIG. 13 (A and B) is a set of two graphs showing the effect of AOL treatment on pulmonary arterial pressure and heart remodeling.

FIG. 14 (A to C) is a set of graphs showing the effect of AOL on pulmonary arteries (PA) remodeling. The effect of AOL (hatched columns) on PA remodeling was assessed by measuring the percentage of PA medial thickness in normoxic rats (N, white columns), chronic hypoxic rats (CH, light grey columns) and monocrotaline-treated rats (MCT, dark grey columns). Intraacinar arteries observed to estimate PA remodeling were separated into three groups with different cross-sectional diameters.

FIG. 15 (A and B) is a set of graphs showing the effect of AOL on the thickness of the outer nuclear layer (ONL) of the retina, in progressive light-induced retinal degeneration.

FIG. 16 (A to C) is a set of graphs showing a lifespan SOD2-KO experiment on four groups of mice (WT-KOL: wild-type mice treated with vehicle; WT-AOL: wild-type mice treated with AOL; KO-KOL: SOD2-KO mice treated with vehicle; KO-AOL: SOD2-KO mice treated with AOL). Data are expressed as mean values.

FIG. 18 (A to C) is a set of graphs showing Oil Red O staining of liver slices from WT and SOD2-KO mice, treated or not with AOL.

EXAMPLES

Figure 1A:
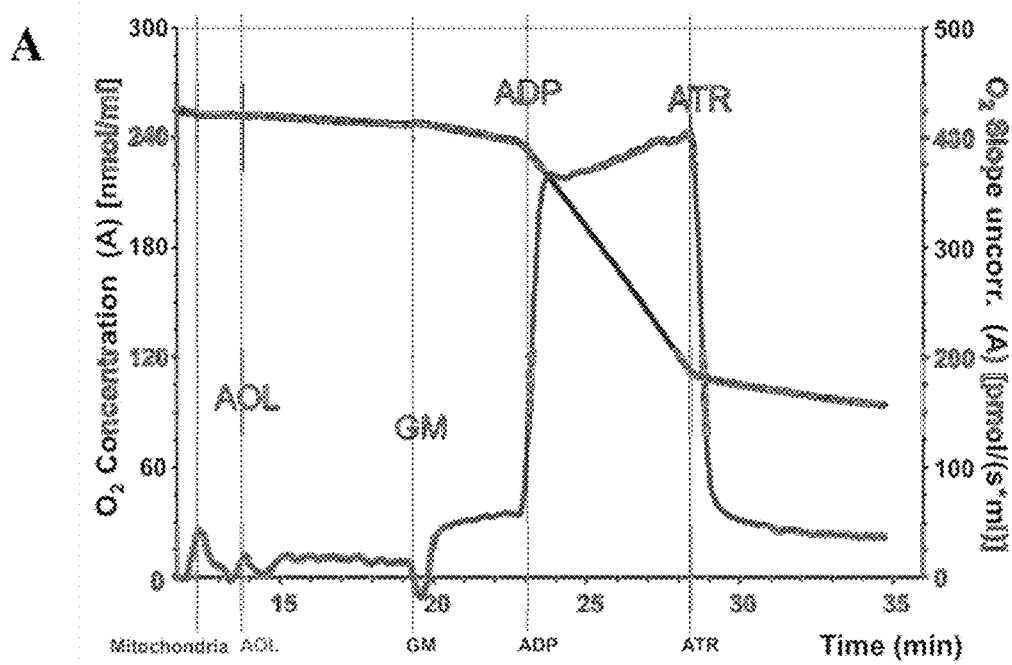
FIG. 1A: After incubation in the presence of AOL (20 µM in this example), isolated mitochondria from rat heart were oxidizing glutamate+malate (GM) as substrate. Phosphorylation was triggered by adenosine diphosphate (ADP) and stopped by Atractyloside (ATR), a specific inhibitor of adenine translocator.

The present invention is further illustrated by the following examples.

Example 1: AOL does not Affect Mitochondrial Oxidative Phosphorylation

Material and Methods
Animal Procedures and Ethics Statement
All experiments described were carried out in agreement with the National and European Research Council Guide for the care and use of laboratory animals. P. Diolez has a valid license to conduct experiments on animals by the Service Vétérinaire de la Santé et de la Protection Animale of the Ministère de l'agriculture et de la Forêt, France (03/17/1999, license number 3308010).

Materials
All the chemicals were reagent grade, purchased from Sigma Chemical (St. Louis, Mo.), except for sucrose and NADH oxidase (that were obtained from Merck (Darmstadt, Germany)). The trithio-AnethOL compound (AOL) was a gift from the private company GMPO (Paris, France). 15 mM stock solution was prepared in DMSO, and kept in darkness at 0° C. for only few days.

Isolation of Mitochondria
Male Wistar rats (250-325 g; obtained from Janvier Labs, Le Genest-Saint-Isle, France) were killed by stunning and cervical dislocation, and the heart was quickly removed and washed in cold isolation medium containing 100 mM sucrose, 180 mM KCl, 50 mM Tris, 5 mM $MgCl_2$, 10 mM EDTA, and 0.1% (w/v) deffated BSA (pH 7.2).

Isolation of heart mitochondria was performed in a cold chamber. Before homogenization, hearts (about 1.5 g) were minced with scissors and treated for 5 min in 5 mL of the same medium supplemented with protease (2 mg of bacterial proteinase type XXIV per mL of isolation buffer) with stirring. The tissue suspension was poured into a 50-ml glass Potter homogenizer, diluted with 20 mL of isolation buffer, then homogenized for 3 min using a motorized Teflon pestle. The homogenate was filtered through bolting cloth (Sefar Nitex) to remove debris, and centrifuged at 8,000 g for 10 minutes. The resulting pellet was rinsed with 5 mL of isolation buffer, resuspended in 25 mL of the same buffer, then subjected to low speed centrifugation (400 g) for 8 mM. The resulting supernatant was centrifuged twice at 7,000 g for 15 min to yield a washed mitochondrial pellet that was gently resuspended in 150 μL of isolation buffer. Protein concentration was determined by the Bradford method (Sigma, kit # B6916) using BSA as standard. Mitochondria were kept on ice at a final concentration of 40-50 mg/mL for less than 5 h.

Mitochondrial Respiration
Oxygen consumption rates of heart mitochondria (0.1 mg/mL), incubated in the absence or presence of AOL at increasing doses (from 0 to 80 μM final concentration), were recorded polarographically under constant stirring at 25° C. using a high resolution oximeter (Oxygraph-2K, Oroboros Instruments, Austria). The respiration medium consisted in 140 mM sucrose, 100 mM KCl, 1 mM EGTA, 20 mM $MgCl_2$, 10 mM $KH_2PO_4$, and 1 g/L (w/v) BSA essentially fatty acid free (pH 7.2).

Mitochondrial, $ROS/H_2O_2$, Production

Rates of $ROS/H_2O_2$ production from heart mitochondria were assessed through the oxidation of the colorless, non-fluorescent indicator Amplex Red in the presence of exogenous horseradish peroxidase (HRP, EC 1.11.1.7, Sigma). $H_2O_2$ reacts with Amplex Red in a 1:1 stoichiometry, yielding the fluorescent compound resorufin (excitation: 560 nm; emission: 585 nm) which is stable once formed. Fluorescence was measured continuously with a spectro-fluorometer equipped with temperature control and stirring (SAFAS Xenius, Monaco). Isolated mitochondria (0.1 mg/mL) were incubated in the same experimental buffer than previously, supplemented with 15 µM Amplex Red and 10 µg/mL HRP. Glutamate (5 mM)/malate (2.5 mM) together with succinate (5 mM) were used as complex I and complex II substrates, respectively. Experiments were conducted under non-phosphorylating conditions in the presence of 15 µM atractyloside, i.e. under state IV conditions where mitochondrial membrane is maximal. Afterwards, rotenone (1.5 µM), antimycin A (2 µM), and myxothiazol (0.2 µM) were sequentially added to inhibit the redox centers within the electron transfer chain (see FIG. 2), namely sites $I_Q$, $I_F$ (with rotenone), $III_Q$, (with antimycin A) and $III_{QO}$ (with myxothiazol). Assay was finally calibrated with known amounts of $H_2O_2$ (steps of 300 nM), in the presence of all relevant compounds, including AOL. The control test of the absence of effect of AOL on the amplex red assay itself and NAD(P)H oxidase $ROS/H_2O_2$ production was carried out in the absence of cardiac mitochondria and the presence of NAD(P)H oxidase (EC 1.6.3.3, 5 mU/mL, Sigma) and NADH (100 µM) solutions.

Results

Figure 1B:
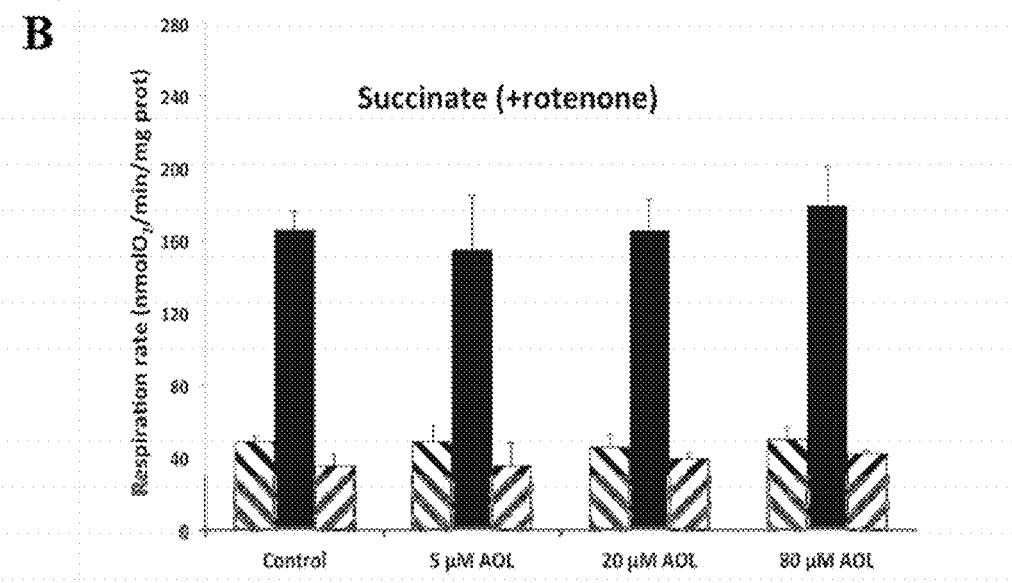
FIG. 1B: The classical study of mitochondrial oxidative phosphorylation in the presence of succinate (+ rotenone) was carried out in the presence of increasing concentrations of AOL (from 5 to 80 µM). There were no statistical differences in mitochondrial respiration under the different energetic states after addition of AOL. Oxidation rate after ADP addition reflects the adenosine triphosphate (ATP) synthesis activity of isolated mitochondria.
Figure 1C:
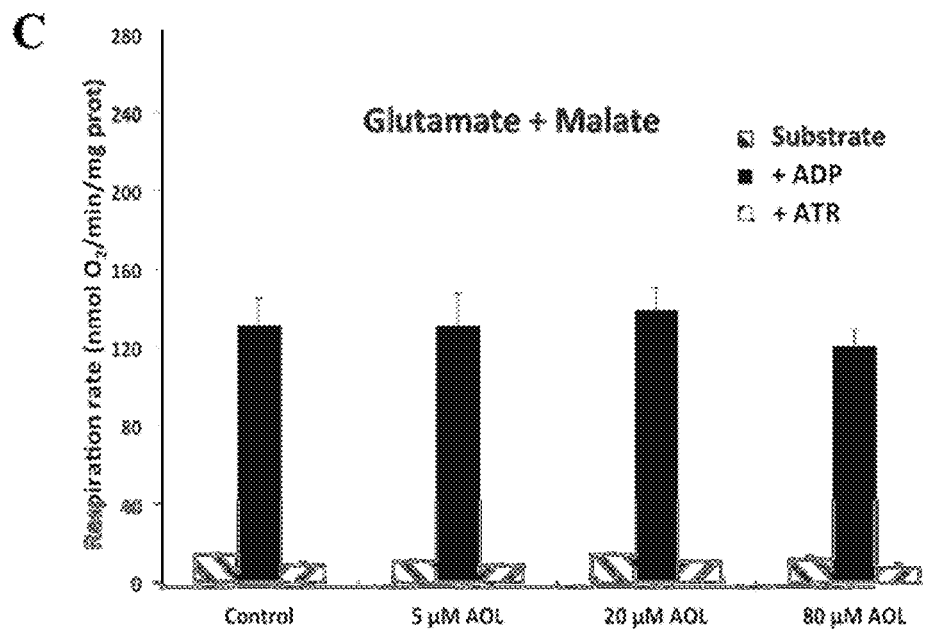
FIG. 1C: The classical study of mitochondrial oxidative phosphorylation in the presence of glutamate and malate was carried out in the presence of increasing concentrations of AOL (from 5 to 80 µM). There were no statistical differences in mitochondrial respiration under the different energetic states after addition of AOL. Oxidation rate after ADP addition reflects the adenosine triphosphate (ATP) synthesis activity of isolated mitochondria.
Figure 1D:
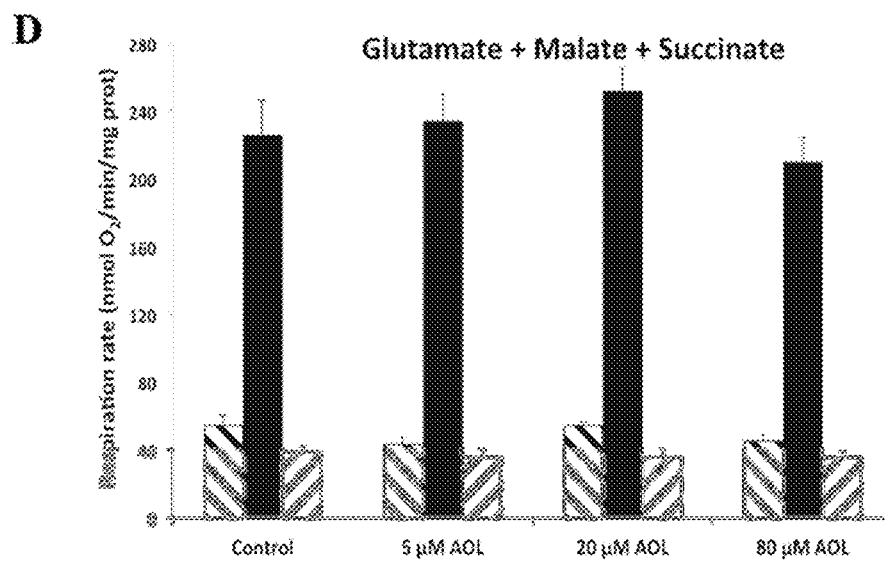
FIG. 1D: The classical study of mitochondrial oxidative phosphorylation in the presence of glutamate, malate and succinate was carried out in the presence of increasing concentrations of AOL (from 5 to 80 µM). There were no statistical differences in mitochondrial respiration under the different energetic states after addition of AOL. Oxidation rate after ADP addition reflects the adenosine triphosphate (ATP) synthesis activity of isolated mitochondria.

We first verified (FIG. 1) that the AOL compound did not affect oxidative phosphorylation directly on isolated mitochondria from rat heart. This has been carried out by using the now classical oxygraph method. Mitochondria were first incubated with various AOL concentrations (5 to 80 µM) then respiratory substrate was added (substrate state, black curve), followed by a saturating ADP concentration to get the maximal oxidative phosphorylation rate (grey curve), and finally the addition of atractyloside (ATR) which inhibits the ADP/ATP translocator and gives the mitochondrial leak rate under non-phosphorylating conditions (FIG. 1A). The other panels of FIG. 1B-D presents the results obtained with different respiratory substrate combinations: glutamate+malate which feed electrons to complex I, succinate (+ rotenone) for complex II and glutamate+malate+succinate to feed electrons to both complexes. This last substrate combination has been chosen since it most closely resembles to in vivo conditions where Krebs cycle functions and both succinate and NADH are oxidized by respiratory chain. The results indicate that statistically no differences were observed in the presence of AOL for the large range of concentrations tested (FIG. 1), demonstrating under these conditions the absence of effect of AOL on mitochondrial oxidative phosphorylation—i.e. both on respiratory chain activity and ATP synthesis—as well as on mitochondrial inner membrane integrity (leak rate, after ATR addition). This last result indicates that AOL does not affect oxidative phosphorylation yield. Together, all these results confirm the absence of any harmful effect of AOL, documented by the use of this drug for human health for a long time.

Example 2: AOL Inhibits Superoxide/$H_2O_2$ Production by Mitochondria

As previously stated, mitochondrial ROS production is highly dependent on mitochondrial activity and conditions. Although we tested the effects of AOL on ROS production by mitochondria under numerous conditions, we chose to present here, for the sake of clarity, only the most demonstrative results of the very specific effects of AOL. As already discussed, the presence of the substrate combination (i.e. Glutamate+Malate+Succinate), giving the electrons to the whole respiratory chain, is the most representative of in situ conditions in the cell where the metabolism is active. Furthermore, maximal mitochondrial $ROS/H_2O_2$ production does not occur under conditions of high mitochondrial phosphorylation but under conditions of high reduction of electron transporters, i.e. low or no phosphorylation. These conditions are fulfilled in the presence of ATR (inhibition of ATP/ADP translocator by ATR, (FIG. 1) and we could effectively verify that the addition of ATR under conditions of saturating ADP triggered the production of ROS which was at the detection limit under maximal phosphorylating conditions (results not shown). Under these conditions, ROS are produced at different sites of the respiratory chain (Orr et al., 2013. *Free Radic. Biol. Med.* 65:1047-1059; Quinlan et al., 2013. *Redox Biol.* 1:304-312) (FIG. 2). The main sites of production are located at complexes I and III, where large changes in potential energy of electrons occur (Balaban et al., 2005. *Cell.* 120:483-495; Goncalves et al., 2015 Jan. 2. *J. Biol. Chem.* 290(1):209-27), which also allow proton pumping at these sites.

Figure 2A:
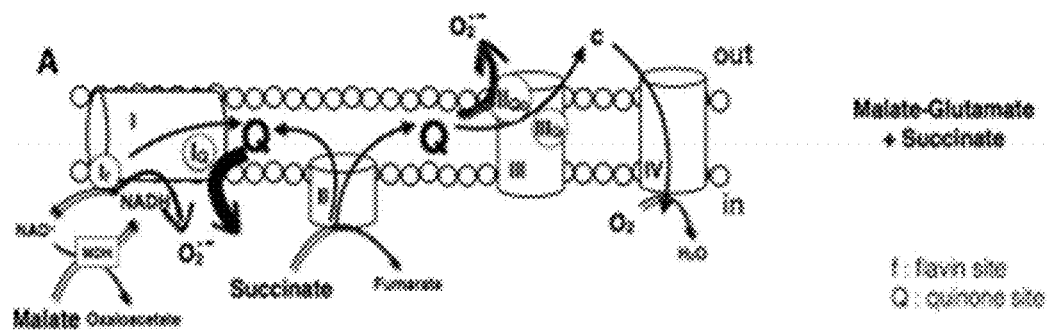
FIG. 2A: production of oxygen radicals by mitochondria in the presence of malate, glutamate and succinate.
Figure 2B:
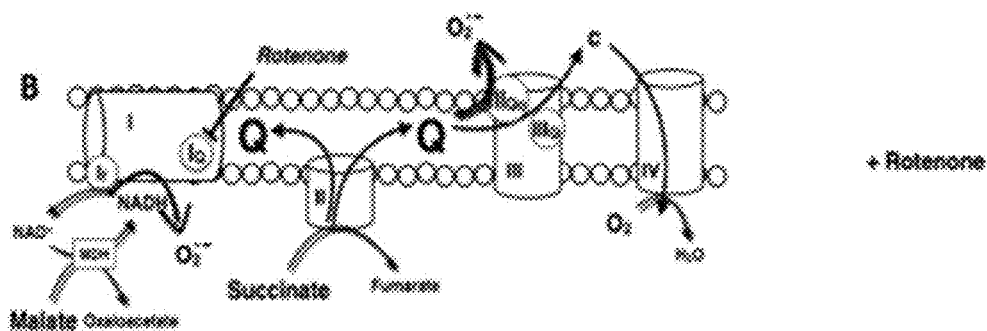
FIG. 2B: production of oxygen radicals by mitochondria in the presence of rotenone.
Figure 2C:
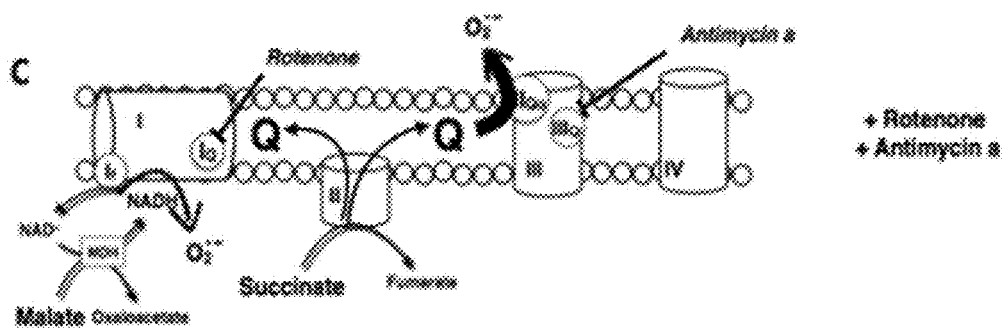
FIG. 2C: production of oxygen radicals by mitochondria in the presence of rotenone and antimycin A.
Figure 2D:
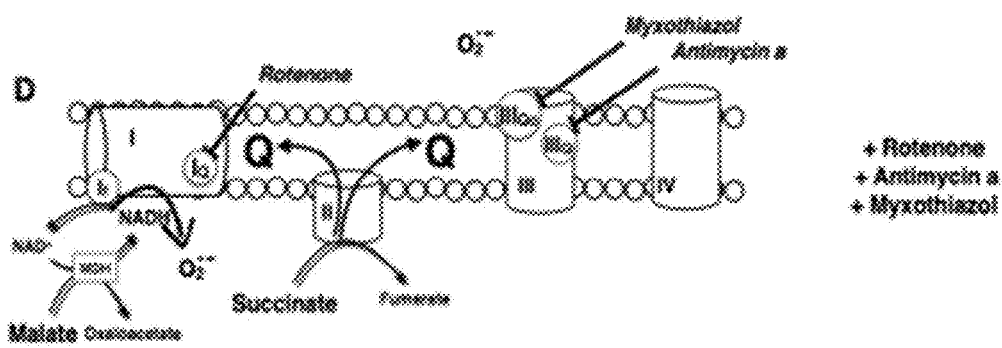
FIG. 2D: production of oxygen radicals by mitochondria in the presence of rotenone, antimycin A and myxothiazol.
Figure 2E:
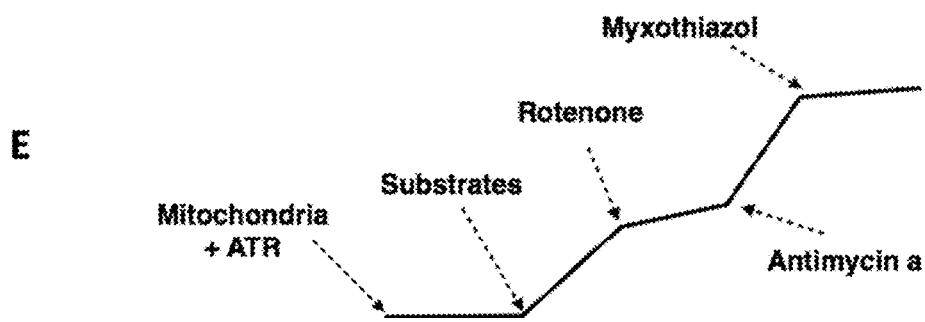
FIG. 2E: chart illustrating the inhibitor titration design implemented to decipher the action of AOL on ROS production by the whole respiratory chain under conditions of maximal ROS production.

We designed a series of inhibitor titrations in order to decipher the action of AOL on ROS production by the whole respiratory chain under conditions of maximal ROS production (FIG. 2E). In the absence of specific inhibitors of the complexes, ROS production is at maximum and mainly comes from reverse electron transport at site $I_Q$ (FIG. 2A). It is crucial to note that ROS produced by complex I, either by site $I_Q$ (quinone site) or site $I_F$ (flavin site), are delivered to the inner—matrix—side of the inner mitochondrial membrane. After addition of rotenone, a classical inhibitor of complex I which specifically binds to $I_Q$, the ROS production decreases strongly and occurs almost entirely at site $III_{QO}$ and a remaining production at site $I_f$ due to the presence of complex I substrates and NADH production which are not inhibited by rotenone (FIG. 2B). The subsequent addition of antimycin A, an inhibitor of the electron transfer to cytochrome c, causes an increase in the reduced over oxidized quinone ratio, which is still reduced by complex II activity, and therefore a concomitant increase in ROS production at site $III_{QO}$ (FIG. 1C). Finally, the addition of myxothiazol, an inhibitor of complex III site $III_{QO}$, abolishes complex III ROS production and the remaining very low production may be ascribed to the flavin site of complex I, for which we have no known inhibitor (Goncalves et al., 2015 Jan. 2. *J. Biol. Chem.* 290(1):209-27).

Figure 3:
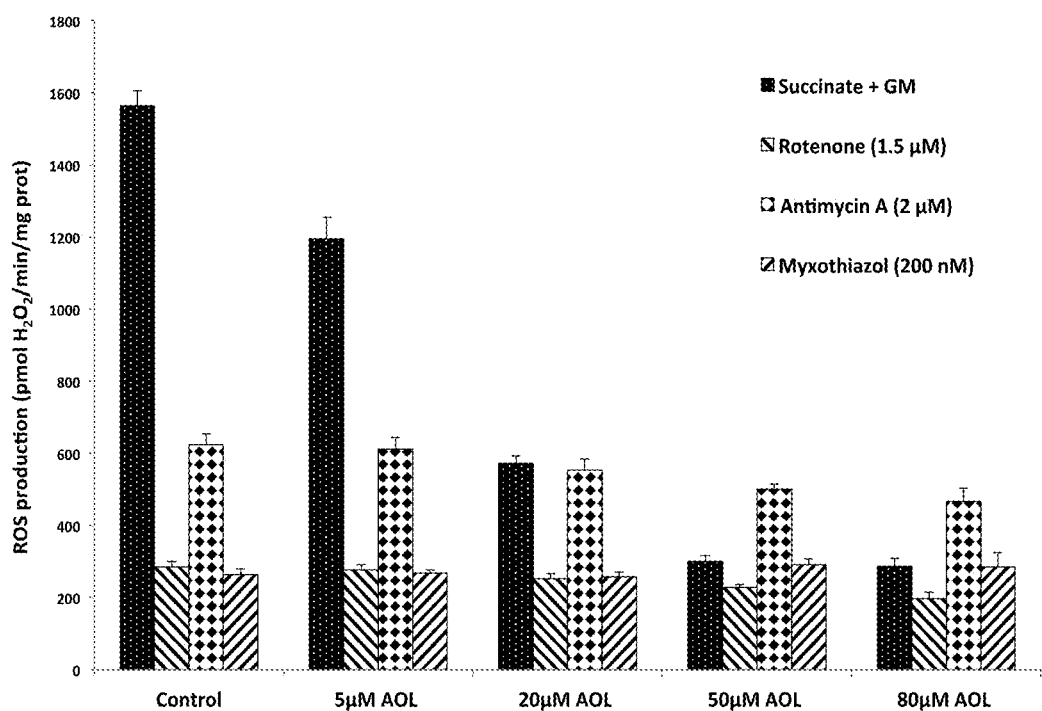
FIG. 3 presents the effect of AOL (5 to 80 µM) on ROS/$H_2O_2$ production by isolated mitochondria in the presence of substrates of complexes I and II in the presence of ATR (state 4), effect of rotenone, antimycin A and myxothiazol. In the absence of specific inhibitors of the complexes, ROS production is at maximum and mainly comes from reverse electron transport at site $I_Q$ (see FIG. 4). After addition of rotenone, which specifically reverse electron transport by inhibiting $I_Q$, production decreases and occurs almost entirely at site $III_{QO}$. The subsequent addition of Antimycin A, which blocks the transfer of the electrons to oxygen, increases ROS production at site $III_{QO}$ and finally myxothiazol blocks ROS production at site $III_{QO}$ (see FIG. 2 for details).

FIG. 3 illustrates the effect of the presence of increasing concentrations of AOL (from 5 to 80 µM) on $ROS/H_2O_2$ production measured under the different conditions defined in FIG. 2. It clearly appears from the results presented in this figure that AOL only affects the ROS production measured in the absence of inhibitor, by approximately 80%, while no statistical differences were observed with this range of AOL concentrations on $ROS/H_2O_2$ measured under the other conditions. As can be seen on FIG. 2, this specific condition (only ATR present) is the only condition in our assay where ROS are produced by complex I (site $I_Q$). When rotenone is added to the assay, ROS/$H_2O_2$ production appears insensitive to AOL, even at high concentrations, whatever the site being involved. The clear absence of effect on several sites of mitochondrial ROS production is not only surprising but also asks interesting questions about the very mechanism of action of AOL on mitochondria. Indeed, these results rule out the basic hypothesis of the mode of action of AOL described in the previous papers and at the basis of the patent for its therapeutic use. These results effectively demonstrate that AOL is not a radical scavenger; otherwise its action would be independent of the origin of the ROS. However, since AOL clearly strongly decreases ROS production by complex I at site $I_Q$, and only that site, we have the evidence that AOL specifically inhibits the formation of ROS at this site.

Although the mechanism has still to be investigated, evidence is presented here that AOL compound specifically interferes with mitochondrial complex I and selectively inhibits superoxide production from the ubiquinone-binding site of complex I (site $I_Q$) with no effects on superoxide production from other sites or on oxidative phosphorylation. To our knowledge, there is only one compound with comparable properties that has recently been described, the N-cyclohexyl-4-(4-nitrophenoxy) benzenesulfonamide (Orr et al., 2013. Free Radic. Biol. Med. 65:1047-1059). Like AOL, this compound does not modify the activity of complex I as a component of the respiratory chain and oxidative phosphorylation.

Figure 4:
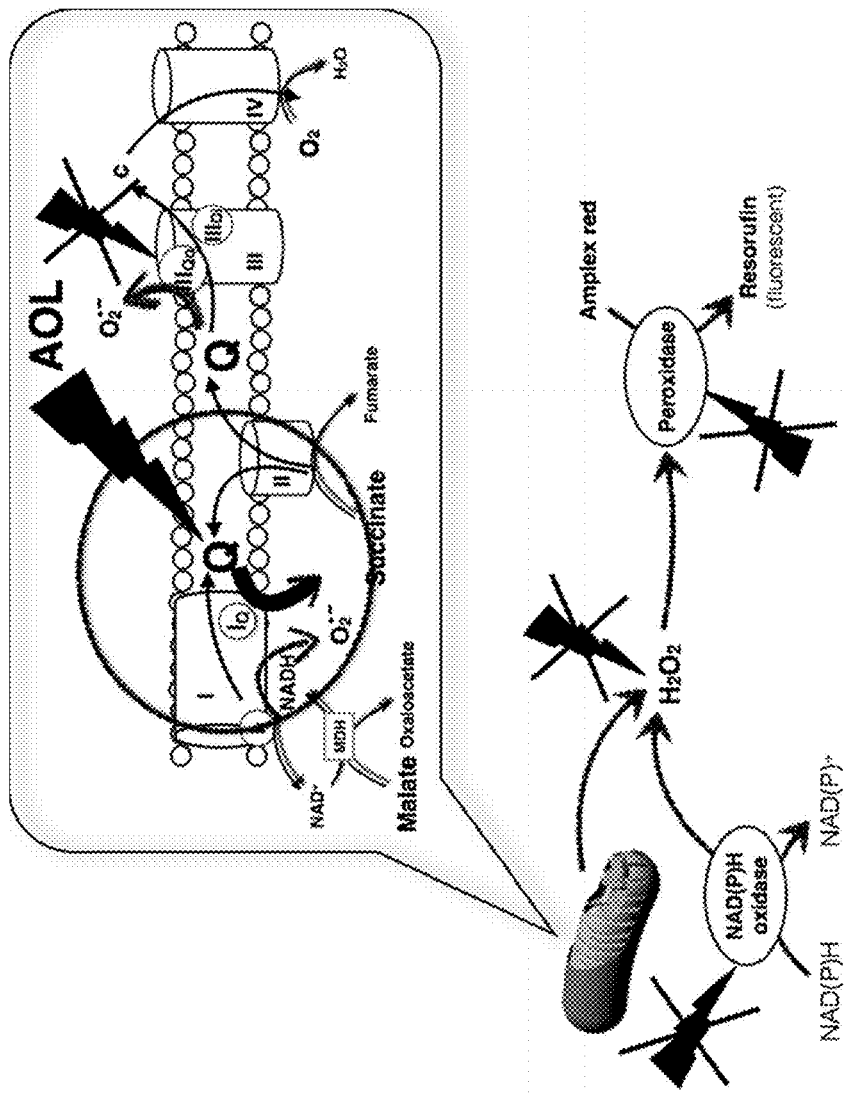
FIG. 4 is a scheme presenting the site of action of AOL on mitochondria ROS production and the sites where AOL has no or little action.

The specificity of AOL was further tested in vitro using the peroxidase-Amplex red system utilized for the measurement of ROS/$H_2O_2$ by mitochondria, which in fact measures the appearance of $H_2O_2$ by the oxidation of amplex red to the fluorescent resorufin (see FIG. 4). In the absence of mitochondria and by adding instead a $H_2O_2$-producing system to the measuring system, it was possible to test the effect of AOL on this system. This has been carried out by using commercial NAD(P)H oxidase which produces $H_2O_2$ in the presence of added NAD(P)H and measuring the reduction of Amplex red to resorufin (FIG. 4). We did not observe any inhibition of the fluorescence under these conditions, which exclude any effect of AOL on the NAD(P)H oxidase or on the peroxidase activity (results not shown). These results confirm that AOL does not interfere either with the measurement system or directly interact with $H_2O_2$. Interestingly, these results also demonstrate that AOL does not inhibit the ROS/$H_2O_2$ production by the NADP(H) oxidase, which is one—if not the—major non-mitochondrial ROS/$H_2O_2$ producer in the cells. The scheme on FIG. 4 recapitulates the different informations on the mode of action of AOL on ROS/$H_2O_2$ production by mitochondria and NAD(P)H oxidase and stresses the very high specificity demonstrated here. These results are in striking contrast with previous assertions on the putative effect of AOL as radical scavenger.

When tested on isolated mitochondria from rat heart, AOL effectively decreases mitochondrial ROS/$H_2O_2$ production (in isolated mitochondria, $H_2O_2$ is produced from the reduction of ROS by mitochondrial superoxide dismutase). However, the results presented here clearly demonstrate that AOL does not act as a simple antioxidant or radical scavenger. While antioxidants are general ROS/$H_2O_2$ scavengers, AOL presents a complete selectivity towards the formation of ROS by site $I_Q$ in complex I, which demonstrates that AOL does not simply interact with superoxide radicals but specifically prevents their formation in complex I. In that respect, AOL therefore appears as a member of a brand new class of oxidative stress protectants, whose only one member has been described very recently (Orr et al., 2013. Free Radic. Biol. Med. 65:1047-1059). Whereas antioxidants generally do not interfere directly with electron transport and scavenge ROS and/or $H_2O_2$ downstream from production and therefore can never fully suppress the effect of ROS (Orr et al., 2013. Free Radic. Biol. Med. 65:1047-1059), AOL may act differently by preventing ROS formation and thus being more active to protect mitochondria from their own ROS.

Data presented here go further and demonstrate that AOL is a specific inhibitor of ROS formation at site $I_Q$ of complex I of mitochondrial respiratory chain. Further experiments are however required to ascertain that AOL has completely no effect on other mitochondrial sites, but this does not preclude the above conclusions. We also show here some evidences that AOL may only interact with mitochondria without affecting oxygen radicals formation in cytosol, and therefore would not affect intracellular signalisation.

Inhibition of complex I activity by rotenone or the neurotoxin MPP has been linked to parkinsonism in both rodents and humans, suggesting a link between dysfunctional complex I, ROS production, and neurodegeneration (Langston et al., 1983. Science. 219:979-980; Betarbet et al., 2000. Nat. Neurosci. 3:1301-1306). In contrast, comparative analyses show an inverse relationship between maximal superoxide/$H_2O_2$ production from site $I_Q$, but not site $I_F$, and maximum life span across diverse vertebrate species (Lambert et al., 2007. Aging Cell. 6:607-618; Lambert et al. 2010. Aging Cell. 9:78-91). Therefore, selective modulators of superoxide/$H_2O_2$ production from site $I_Q$ or site $I_F$ would offer unique opportunities to probe the putative role of mitochondrial ROS production in normal and pathological processes (Orr et al., 2013. Free Radic. Biol. Med. 65:1047-1059). There are also some speculations, even controversial, that site $III_{Qo}$—not affected by AOL—play an important role in cellular signalling during hypoxia.

In conclusion, it appears that AOL properties may represent a breakthrough in the search for specific modulators of ROS/$H_2O_2$ production in cells. This is a current important issue in research, and AOL has an enormous advantage toward newly discovered molecules since it is already authorized for human use.

- AOL acts upstream from ROS production, therefore insuring higher protection than classical antioxidants;
- AOL acts specifically on mitochondrial ROS production;
- AOL ensures mitochondrial protection, crucial for numerous diseases, especially cardiac ones;
- AOL does not interfere with cell signalisation;
- AOL acts specifically on site $I_Q$ in complex I, which is the main mitochondrial site and may be implicated in important diseases, including Parkinson's disease and cardiac fibrillation.

→AOL may represent the first member of a new class of "protectants" that specifically prevent ROS production inside mitochondria, and may therefore be used for mitochondrial protection during various oxidative stress and therefore prevent diseases, with very little side effects on crucial cellular ROS signalling.

Example 3: Effect of AOL in a Cardiovascular Disease: Diabetes

Effect of the Compound AOL on Glucose-Stimulated Insulin Secretion (GSIS) in Mouse Pancreatic Islets The aim of the study was to investigate the ability of the compound AOL in modulating glucose-stimulated insulin secretion (GSIS) in isolated pancreatic islets from mice.

Material and Methods

Experiments were conducted in strict compliance with the European Union recommendations (2010/63/EU) and were approved by the French Ministry of Agriculture and Fisheries (authorization n° 3309004) and the local ethical committee of the University of Bordeaux. Maximal efforts were made to reduce the suffering and the number of animals used.

Three independent experiments were carried out and, for each of them, two mice were sacrificed and islets isolated according to the procedure further described below.

Pancreatic islets were isolated using the collagenase digestion method. Briefly, pancreas was inflated with Hanks solution containing 0.33 mg/mL of collagenase (Sigma-Aldrich), 5.6 mM glucose and 1% bovine serum albumin, pH 7.35, removed and kept at 37° C. for 6-9 minutes. After tissue digestion and exocrine removal by three consecutive washes, the islets were manually collected, under a binocular magnifier. Islets were left recovering from digestion by culturing for 20-24 hours in RPMI-1640 medium containing 11 mM glucose (Invitrogen, Calif., USA) and supplemented with 2 mM glutamine, 200 IU/mL penicillin, 200 μg/mL streptomycin and 8% fetal bovine serum stripped with charcoal-dextran (Invitrogen).

For each static GSIS experiment, islets from two mice were first incubated for 2 hours at 37° C. in 3 mL Krebs-bicarbonate buffer solution (in mM): 14 NaCl, 0.45 KCl, 0.25 $CaCl_2$, 0.1 $MgCl_2$, 2 HEPES and 3 glucose, equilibrated with a mixture of 95% $O_2$:5% $CO_2$, pH 7.4. Then, groups of five size-matched islets were transferred to 24-well plate wells with 0.5 mL fresh buffer containing either one of the following stimulus: 3 mM glucose (Glc) and 11 mM glucose plus vehicle (0.4% DMSO in Krebs-bicarbonate buffer), or 11 mM glucose plus the diluted drug to be tested (10 μM or 20 μM of AOL in vehicle), and further incubated for 1 hour. Six different wells were used for each experimental condition. At the end of the incubation, bovine albumin was added to each well to a final concentration of 1%, and the plate was put at 4° C. for 15 minutes to stop insulin secretion. Next, the media was collected and stored at −20° C. for subsequent measurement of insulin content by ELISA (kit from Mercodia, Uppsala, Sweden), according to the manufacturer's instructions. Insulin secretion in each well was calculated as ng of insulin per islet and per hour of incubation, and then expressed as percentage of insulin secretion in 11 mM glucose vehicle group, which was considered 100%.

Description of the experimental groups is shown in Table 1.

TABLE 1

| | Group abbreviation | | | |
|---|---|---|---|---|
| | 3 mM Glc-Veh | 11 mM Glc-Veh | 11 mM Glc + AOL 10 μM | 11 mM Glc + AOL 20 μM |
| Group definition | Group treated with vehicle and 3 mM glucose | Group treated with vehicle and 11 mM glucose | Group treated with AOL 10 μM and 11 mM glucose | Group treated with AOL 20 μM and 11 mM glucose |
| Number of wells | 4-6 | 5-6 | 4-6 | 6 |

Results

Figure 5:
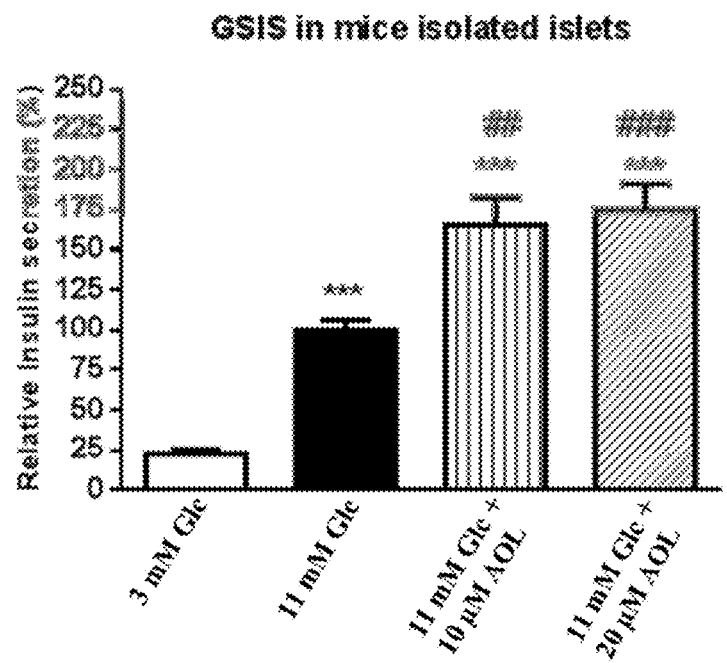
FIG. 5 is a histogram showing the effect of 10 and 20 µM AOL on glucose stimulated insulin secretion (GSIS) in isolated islets from male C57Bl/6J mice. Combination of three experiments is displayed. Islets from two mice for each experiment; five islets each well; four to six wells each condition. Insulin secretion data were normalized to 11 mM Glc-Veh group, which was considered 100%. *p<0.05, p<0.01 and *p<0.001 versus 3 mM Glc-Veh; # p<0.05, ## p<0.01 and ### p<0.001 versus 11 mM Glc-Veh; One-way ANOVA and Bonferroni's post-hoc test.

Individual insulin secretion values obtained in each of the three experiments were combined and averaged. These are expressed as the relative percentage of insulin secretion, normalized to the 11 mM glucose vehicle group (FIG. 5).

Combined analysis of data shows that AOL enhanced GSIS at both 10 and 20 μM, showing a similar potency, with a GSIS increase ranging around 65-75% as compared to the 11 mM glucose vehicle group (One-way ANOVA; Bonferroni's post-test). For statistical analysis see Table 2.

TABLE 2

| | One-way ANOVA | Sum of squares | Degrees of freedom | Mean of squares | F | P |
|---|---|---|---|---|---|---|
| Experiment #1 | Treatment | 50630 | 3 | 16880 | 18.36 | <0.0001 |
| | Residual | 16540 | 18 | 919.0 | | |
| Experiment #2 | Treatment | 44790 | 3 | 14930 | 21.46 | <0.0001 |
| | Residual | 12530 | 18 | 695.9 | | |
| Experiment #3 | Treatment | 193700 | 3 | 64570 | 35.16 | <0.0001 |
| | Residual | 33060 | 18 | 1837 | | |
| Combined experiments | Treatment | 244100 | 3 | 81360 | 33.13 | <0.0001 |
| | Residual | 152200 | 62 | 2455 | | |

Conclusion

The study demonstrates that AOL, at the doses tested (10 and 20 μM), enhances GSIS and significantly stimulates insulin secretion in vitro, in isolated pancreatic islets from mice.

Thus, these findings suggest that AOL might be particularly useful in pathological conditions in which insulin secretion is deficient.

Effects of a Chronic Treatment with AOL on Food Intake, Body Weight and Glucose Metabolism in Diet-Induced Obese Mice Material and Methods The aim of the study was to determine whether the compound AOL, administered daily at the doses of 5 mg/kg and 10 mg/kg for up to five weeks by intraperitoneal (ip) daily administration in diet-induced obese (DIO) mice fed with a high-fat diet (HFD), modifies food intake, body weight, adiposity and glucose metabolism.

Mice were fed ad libitum with a HFD (60% of calories from fat, mostly lard) for twelve weeks before the pharmacological study begun. Animals received AOL or its vehicle by intraperitoneal (ip) administration and were maintained on HFD for the length of the study. Food intake and body weight were measured daily and recorded for up to three consecutive weeks.

For appropriate distribution of the mice in the different experimental groups before the start of the pharmacological study, we evaluated their body composition in vivo using an Echo MRI 900 (EchoMedical Systems, Houston, Tex., USA) (see also Cardinal P. et al., 2014 October Mol. Metab. 3(7):705-16; Cardinal P. et al., 2015 February Endocrinology. 156(2):411-8). Daily food intake and body weight measurements were obtained using a balance (model TP1502, Denver Instruments).

Thirty 7-weeks-old male C57/Bl6J mice arrived to the laboratory on 25 Feb. 2016 and underwent a first in vivo body composition analysis (Echo MRI 900, EchoMRI Systems) after 1 week of adaptation to the experimental housing room. After this first MRI analysis, animals were fed a high-fat diet (HFD) ad libitum for a period of twelve weeks. Thereafter, they underwent a second MRI analysis and were distributed into 3 experimental groups of equivalent body weight and body composition.

Once the pharmacological treatment started (day 1), food intake (FI) and body weight (BW) were measured daily before the dark phase in animals housed in their home cage. Spillage of food was checked daily. The food consumed was calculated by subtracting the food left in the hoppers from the initial pre-weighted amount. H and BW were measured for three consecutive weeks. Afterwards animals underwent a third MRI analysis in order to observe potential effects of the treatment onto the body composition (changes in fat and lean mass), followed by a glucose tolerance test (GTT) and an insulin tolerance test (ITT). Mice received daily ip administration of AOL or its vehicle for a total length of five weeks, until they were sacrificed.

A nuclear echo magnetic resonance imaging whole-body composition analyzer (Echo MRI 900; EchoMedical Systems) was used to repeatedly assess body fat and lean mass in conscious mice.

GTT and ITT are routinely used to assess dynamic modulation of glucose metabolism respectively during a glucose challenge and an insulin challenge. They give information on the presence of glucose intolerance and possible resistance to the action of the hormone insulin.

Animals were injected ip with 1.5 g/kg of D-Glucose (Sigma-Aldrich) for the GTT or with 0.5 U/kg of insulin (Humulin, Lilly, France) for the ITT. For the GTT and the ITT, animals were fasted overnight. The tests were conducted the following morning. Blood samples were taken from the tail vein at different time points (0, 15, 30, 60, 90 and 120 minutes after the ip administration of glucose or insulin) and glucose concentration was measured using glucose sticks (OneTouch Vita, Lifescan France, Issy les Moulineaux, France).

At sacrifice, blood samples were collected, blood glucose was rapidly assessed using glucose sticks and blood samples were then centrifuged at 3000 rpm for 15 minutes. The obtained plasma was stored at −80° C. for subsequent measurement of insulin, which was carried out by performing an ELISA (kit from Mercodia, Uppsala, Sweden), according to the manufacturer's instructions.

HOMA-IR index, which gives information about the presence of insulin resistance, was calculated using the formula (Glucose mmol/L×Insulin mU/L)/22.5.

Statistical analyses were carried out using GraphPad Prism Software (San Diego, Calif., USA). Repeated measurements two-way ANOVA were carried out to analyze the effects of the treatment factor, the time factor and their interaction on food intake, body weight, GTT and ITT. One-way ANOVA was carried out to compare the effect of the treatment factor on cumulative food intake, body composition, AUC of GTT and ITT, and circulating glucose, insulin and HOMA-IR at time of sacrifice. When ANOVA results were significant (p<0.05), the Tukey post-hoc test was performed to allow adequate multiple comparisons among the groups. Data are expressed as mean±SEM. Graphs were generated using GraphPad Prism software.

Results

The treatment did not have a significant effect on body weight or on the percentage (%) of change of the body weight calculated from day 1 in which body weight was measured before the first administration of AOL.

Figure 6:
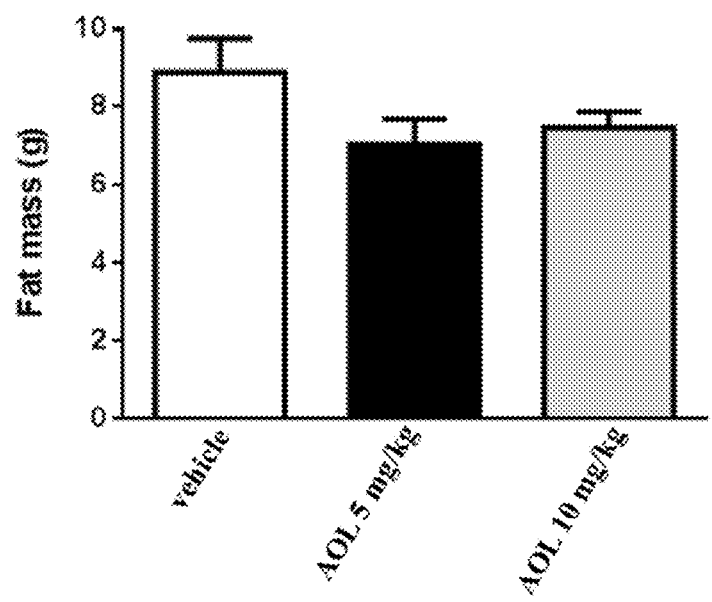
FIG. 6 is a histogram showing the fat mass determined after 3 weeks of treatment. Fat mass is expressed in grams (g). Data are expressed as mean±SEM.
Figure 7:
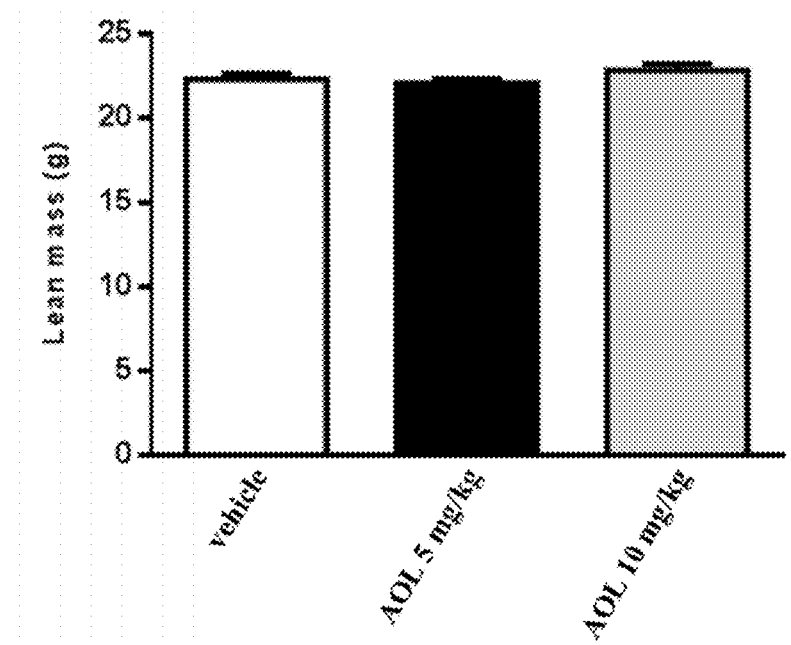
FIG. 7 is a histogram showing the lean mass determined after 3 weeks of treatment. Lean mass is expressed in grams (g). Data are expressed as mean±SEM.

Chronic administration of AOL after three weeks tended to reduce fat mass (p=0.13, FIG. 6), whilst it did not have any effect on lean mass (FIG. 7). The mean±SEM values are represented in FIG. 6 and FIG. 7 and statistical analysis are shown in Table 3 and Table 4, respectively.

TABLE 3

Statistical analysis of data represented in FIG. 6.

| One-way ANOVA | Sum of squares | Degrees of freedom | Mean of squares | F | p |
|---|---|---|---|---|---|
| Treatment | 18.50 | 2 | 9.248 | 2.151 | 0.1366 |
| Residual | 111.8 | 26 | 4.299 | | |

TABLE 4

Statistical analysis of data represented in FIG. 7.

| One-way ANOVA | Sum of squares | Degrees of freedom | Mean of squares | F | p |
|---|---|---|---|---|---|
| Treatment | 2.773 | 2 | 1.387 | 1.256 | 0.3014 |
| Residual | 28.70 | 26 | 1.104 | | |

AOL at the dose of 10 mg/kg significantly blunted the action of insulin on circulating glucose levels during an ITT (FIG. 8), suggesting the presence of insulin resistance. Accordingly, a treatment effect was also found when analyzing the AUC (AUC veh: 12812.50±750.35, AUC AOL 5 mg/kg: 15006.56±1139.69, AUC AOL 10 mg/kg: 18168.33±1562.90, one-way ANOVA $F(2, 23)=5.186$, p=0.0138), with the AOL 10 mg/kg group having an AUC significantly higher than the vehicle group (Tukey post-hoc, p=0.0107). The mean±SEM values are represented in FIG. 8 and statistical analysis are shown in Table 5.

TABLE 5

Figure 8:
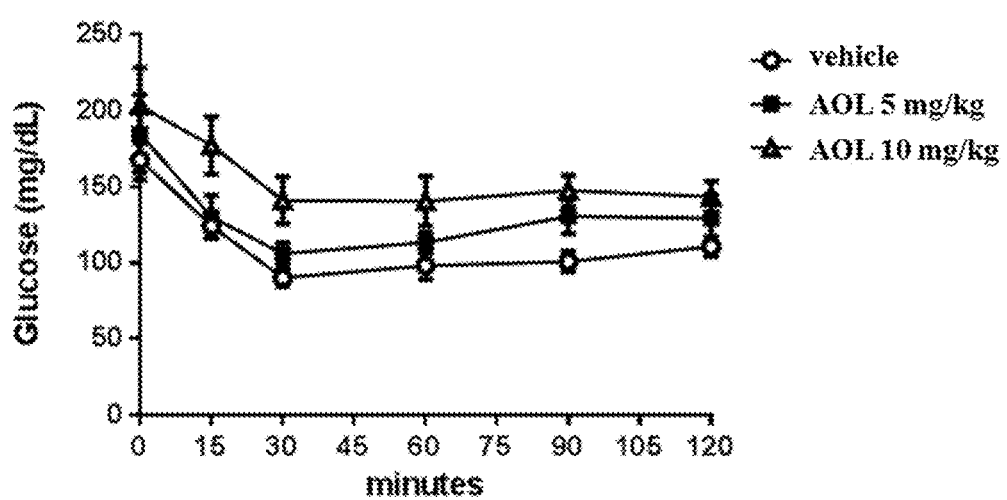
FIG. 8 is a graph showing the effect of chronic treatment with AOL (5 mg/kg and 10 mg/kg) on glucose responses during an insulin tolerance test (ITT). The graph represents changes in blood glucose levels during an ITT. Data are expressed as mean±SEM.

Post-hoc analysis on the treatment factor for data in FIG. 8.

| Tukey post-hoc | Vehicle | AOL 5 mg/kg | AOL 10 mg/kg |
|---|---|---|---|
| Vehicle | | 0.532016 | 0.023546 |
| OP 5 mg/kg | 0.532016 | | 0.232976 |
| OP 10 mg/kg | 0.023546 | 0.232976 | |

The numbers in the Tukey Post-hoc analysis table represent the p values. Values in bold correspond to significant (p < 0.05)results.

At time of sacrifice, after five weeks of treatment, blood glucose levels were measured in 2-hour fasted mice.

AOL tended to decrease blood glucose levels (FIG. 9) and statistical analysis in Table 6.

TABLE 6

Figure 9:
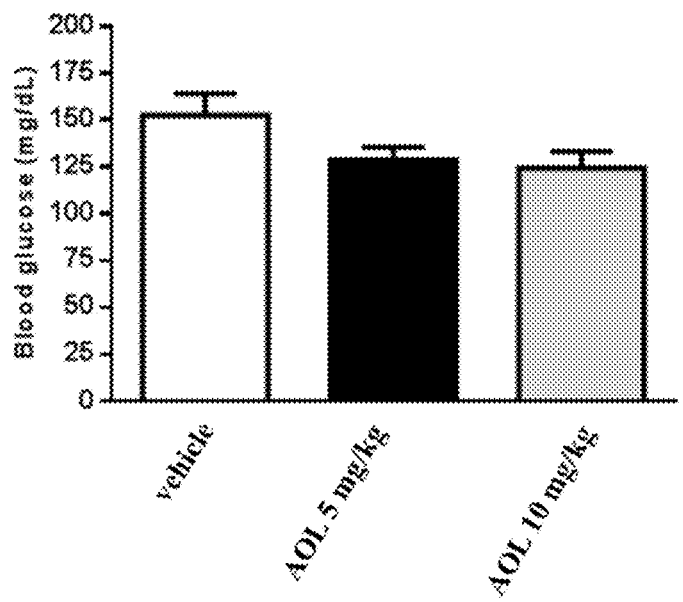
FIG. 9 is a histogram showing the effect of AOL on blood glucose levels. After five weeks of treatment, blood glucose was measured in 2-h fasted mice. Data are expressed as mean±SEM.

Statistical analysis of data represented in FIG. 9.

| One-way ANOVA | Sum of squares | Degrees of freedom | Mean of squares | F | p |
|---|---|---|---|---|---|
| Treatment | 3972 | 2 | 1986 | 2.586 | 0.0980 |
| Residual | 16898 | 22 | 768.1 | | |

Conclusion

In diet-induced obese animals, chronic daily administration of AOL tended to decrease body weight and food intake in DIO mice (data not shown). Accordingly, this was associated with a trend to decrease fat mass and basal blood glucose levels.

Overall, these data suggest that AOL might have some beneficial effects in a model of dietary obesity.

Example 4: Effect of AOL in a Neurologic Disease: Parkinson Disease

In this study, the potential neuroprotective effects of AOL were assessed by counting the number of tyrosine hydroxylase (TH)-positive neurons in the substantia nigra (SN) in the sub-chronic 1-methyl-4-phenyl-1,2,3,6-tetrahydropyridine (MPTP) mouse model of Parkinson's disease. Mice were treated with AOL (5 mg/kg; ip) or vehicle for 11 consecutive days. MPTP (20 mg/kg; ip) or saline was administered on treatment days 4-8. All mice were killed on day 12 following final administration of treatment.

Sub-chronic MPTP administration in C57/bl6 mice induces degeneration of nigrostriatal dopaminergic neurons, which leads to reduced number of TH-positive neurons in the SN which was, on this occasion, a reduction of 39%.

Material and Methods

For vehicle conditions, the test item was dissolved in 0.5% DMSO/0.95% Tween 20 in saline while AOL was administered intraperitoneally (i.p.) at the dose of 5 mg/kg. The volume of administration was 10 mL/kg.

C57bl/6 male mice (Janvier) weighing 22-28 g were housed in a temperature-controlled room under a 12-hour light/dark cycle with free access to food and water. In order to tentatively achieve final numbers of n=10 per group, n=12 per group were be used to account for possible losses in the course of the experiment. To produce neurodegeneration of dopaminergic neurons in the substantia nigra, mice were treated with MPTP hydrochloride (20 mg/kg i.p. once daily for five consecutive days).

Mice were humanely euthanized by cervical dislocation after the last administration.

The caudal half of the brain (containing the substantia nigra) was placed in paraformaldehyde (4% in 0.1 M Phosphate Buffer Saline (PBS) pH 7.4) for 5 days and then transferred to 20% sucrose (20% in 0.1 M PBS) for cryoprotection. The tissue was then frozen in cold isopentane (at $-50°$ C. plus or minus $2°$ C.).

The striata were dissected out, weighed and snap frozen separately in dry ice (at $-70°$ C. plus or minus $10°$ C.). Tissues samples are stored at $-70°$ C. (plus or minus $10°$ C.) for an optional HPLC analysis of dopamine and its metabolites. If this option is not taken, the *striata* will be destroyed.

Coronal serial sections of the entire mesencephalon were cut on a cryostat at 50 µm intervals. Sections were collected free-floating in well-plates containing cryoprotectant solution, which were then stored at $-20°$ C. until the day of TH immunohistochemical processing.

TH immunohistochemistry was performed as follows on every fourth section. Tissue sections were taken from the $-20°$ C. freezer, left to adjust to room temperature, and then rinsed in PBS solution. Endogenous peroxidase was inhibited by incubating in PBS containing 0.3% $H_2O_2$ for 10 minutes. Following this, sections were washed in PBS, incubated in PBS 4% normal horse serum (NHS) and 0.3% Triton X-100 for 30 minutes, for the blockade of non-specific antigenic sites. Sections were then incubated overnight at room temperature in antibody dilutant+primary antibody for tyrosine hydroxylase (TH) (anti-TH affinity isolated antibody, Sigma T8700) at a dilution of 1/10,000. Sections were then rinsed thoroughly in PBS and incubated for 30 minutes in ImmPRESS Ig peroxidase polymer detection reagent (Vector MP7401). Following this, sections were thoroughly washed with PBS Immunological staining was then revealed with 3,3'-Diaminobenzidine (DAB)/Tris/$H_2O_2$ kit (Vector SK4100). After one minute, revelation was stopped with several PBS washes. Sections were mounted and counterstained with 0.1% cresyl violet.

Unbiased stereological analysis was used to estimate the number of TH-immunopositive (TH+) neurons (Mercator, Explora Nova, La Rochelle, France). The boundaries of the SN were determined by examining the size and shape of the different TH+ neuronal groups. The volume was calculated by using the formula: V=ΣS td; where ΣS is the sum of surface areas, t is the average section thickness and d is the number of slices between two consecutive sections measured. One in every 4 sections was used; optical dissectors were distributed using a systematic sampling scheme. Dissectors (50 µm length, 40 µm width) were separated from each other by 150 µm (x) and 120 µm (y). The following formula was used to estimate the number of TH+ neurons: N=V(SN) (ΣQ-/ΣV(dis)); where N is the estimation of cell number, V is the volume of the SN, ΣQ- is the number of cells counted in the dissectors, and ΣV(dis) is the total volume of all the dissectors. Mean estimated number of neurons and SEM was then calculated for each group All statistical analyses were performed using Graphpad prism version 7. All data are presented as mean±the standard error of the mean (SEM). The effect of AOL was analysed with a one-way ANOVA followed by Dunnett's multiple comparisons post-hoc analysis. A P value of less than 0.05 was considered significant.

Results

Figure 10:
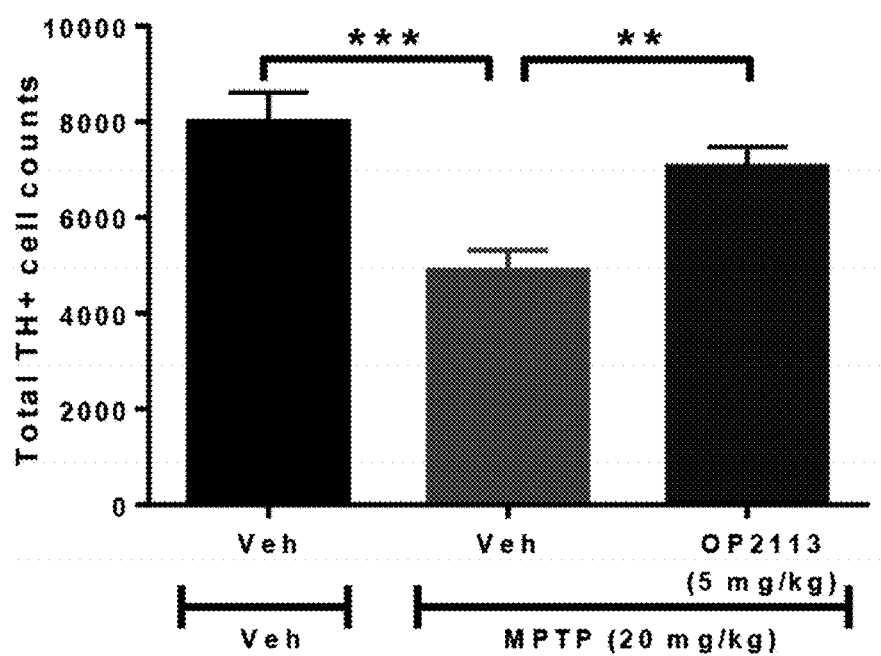
FIG. 10 is a histogram showing the neuroprotective effect of AOL (5 mg/kg bid for 11 days) on TH-positive cell counts in the SN in MPTP-treated mice. Data expressed as mean±SEM (n=10-11) and analyzed using one-way repeated measures ANOVA followed by Dunnett's multiple comparison test. P<0.01;*P<0.001 c.f. MPTP+vehicle.

There was a significant effect of treatment on the number of TH+ cells in the SN ($F_{2,29}=10.94$, $p<0.001$, FIG. 10). The number of TH+ cells in the SN was reduced by 39% ($p<0.001$) in MPTP-treated compared to vehicle-treated animals. Following administration of AOL, the number of TH+ cells in the SN was increased by 44% ($p<0.01$) compared to vehicle in the MPTP-treated mice.

Conclusion

AOL treatment for 11 consecutive days, at a dose of 5 mg/kg, has a significant neuroprotective effect compared to vehicle, in preventing the MPTP-induced reduction in TH+ cells in the SN, resulting in 44% more cells surviving in the SN with the administration of AOL.

These data suggest that AOL treatment can protect the dopaminergic neurons in the substantia nigra from MPTP intoxication.

Example 5: Effect of AOL in Cardiovascular Disease: Ischemia-Reperfusion Injury

The present study aims at evaluating the capacity for AOL to protect perfused rat heart from the damages occurring after global ischaemia and reperfusion.

The consequences of 30 minutes' global ischaemia followed by 120 minutes' reperfusion (FIG. 11) on contractility and tissue viability were studied on isolated perfused rat heart pretreated or not (control vehicle) with 10 µM AOL.

Material and Methods

All procedures conformed to the UK Animals (Scientific Procedures) Act 1986 and the Guide for the Care and Use of Laboratory Animals published by the National Institutes of Health (NIH Publication No. 85-23. revised 1996). Male Wistar rats (250-300 g) were anesthetized by 3% isoflurane, heparinized and euthanized by a lethal IP injection of pentobarbital (130 mg/kg). Hearts (~0.95 g of fresh weight) were rapidly harvested and placed into ice cold Krebs-Henseleit buffer containing (in mmol/L): NaCl 118, NaHCO$_3$ 25, KCl 4.8, KH$_2$PO$_4$ 1.2, MgSO$_4$ 1.2, glucose 11 and CaCl$_2$ 1.8; gassed with 95% O$_2$/5% CO$_2$ at $37°$ C. (pH 7.4). Langendorff heart perfusions were performed (Garlid, K. D. et al., 2006. *Am. J. Physiol. Heart Circ. Physiol.* 291(1):H152-60) and contractility was assessed by continuous measurement of the rate pressure product (RPP) thanks to a balloon placed in the left ventricle and connected to a pressure transducer. Hearts were perfused in a constant flow mode (12 mL/min). After 10 minutes for stabilization followed by 10 minutes of treatment with the vehicle (Control) or 10 µM AOL solution, global normothermic ischaemia was induced by halting perfusion flow for 30 minutes while immersing the heart in perfusion buffer at 37° C. At the end of the reperfusion period, hearts were stained to assess infarct size, or freeze-clamped using liquid-nitrogen cooled tongues. In the latter case, hearts were grinded under liquid nitrogen, and stored at −80° C. for further analyses.

At the end of the reperfusion period, hearts were stained with triphenyltetrazolium chloride (TTC): hearts were perfused for 7 minutes at 13 mL/min with a 12% (w/v) TTC solution in order to get a 1% final concentration in the heart. Hearts were then detached from the cannula and incubated for an additional 4 minutes at 37° C. before being sliced perpendicular to the longitudinal axis into 6 slices. The slices were then treated in 4% (w/v) formalin solution overnight at 4° C. and weighed, before both sides of each slice were photographed. The surface of the necrotic and at risk areas of each side were determined on each photography by planimetry (AlphaEase v5.5), and infarct size was expressed as a percentage of the total cross-sectional area of the heart, since total heart was subjected to ischemia.

Data from 6 independent preparations are expressed as means±SEM. The n number in each group being smaller than 20, the distribution was considered as non-normal and consequently a non-parametric Mann-Whitney test (SPSS statistics 17.0) was performed to compare the two groups. Results were considered statistically significant if the p-value was below 0.05.

Results

Figure 11:
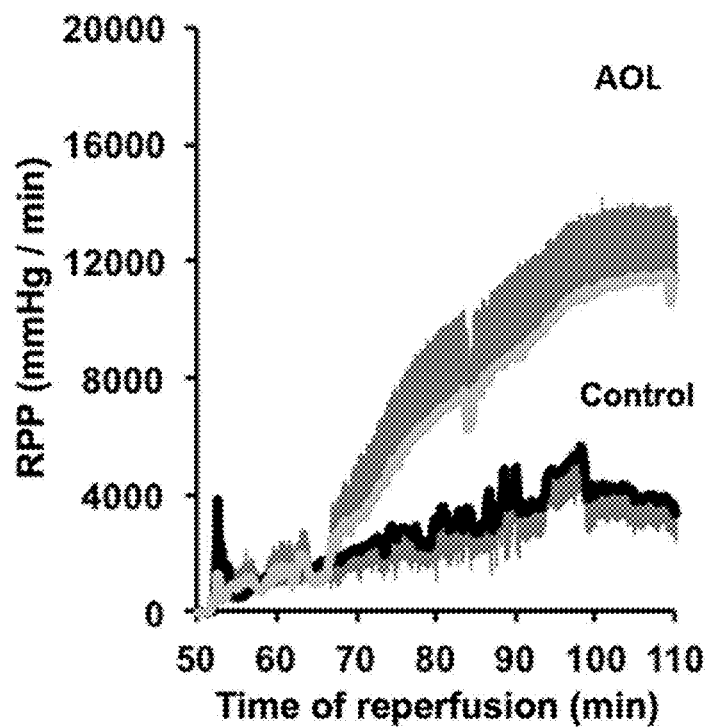
FIG. 11 is a graph showing the effect of AOL on the recovery of heart contractility during the reperfusion phase following ischaemia. Data are expressed as mean±SEM for control (black) and AOL treated (grey) for 6 independent experiments.
Figure 12:
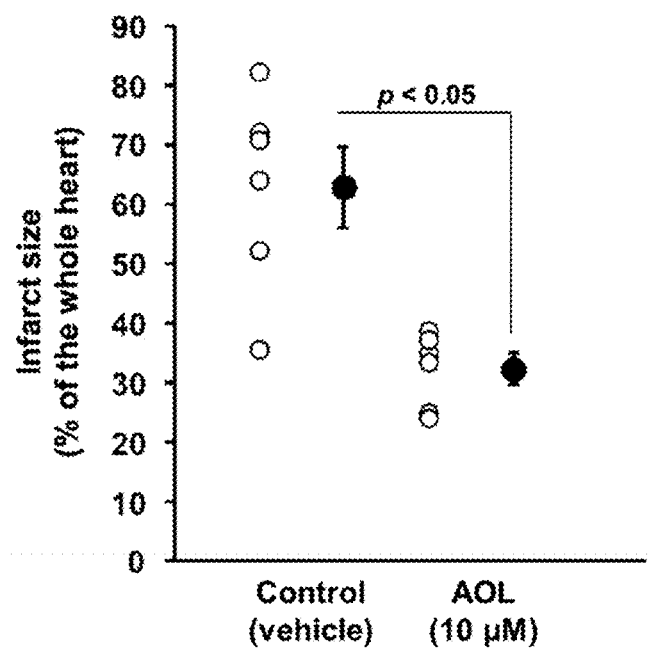
FIG. 12 is a graph showing the effect of AOL on the infarct size of the slices of ischaemic hearts. At the end of the reperfusion period, hearts were stained by triphenyltetrazolium chloride (TTC). Living tissue appears red, while damaged tissue appears white.

FIG. 11 presents the evolution of the RPP—considered here as a surrogate of heart contractility—during the critical phase of the reperfusion following ischaemia. Clearly, AOL improves the contractility and after an identical evolution as compared to the control hearts treated with AOL, showed an improvement of contratility which was about three times higher than control hearts after 2 hours of reperfusion. At this time, hearts were prepared for TTC staining to assess tissue viability. The higher contractile activity for AOL hearts was confirmed by TTC staining, and photographs of the slices of treated and non-treated hearts (data not shown) clearly show that AOL induced an important protection of cardiac tissue. This protection has been analyzed more thoroughly and the results are presented in FIG. 12. The infarct size—damaged tissue—is expressed as percentage of the total surface for each independent experiment together with the mean value for AOL-treated and non-treated hearts. Results clearly show that AOL highly significantly protects cardiac tissue from ischaemia/reperfusion damages. In fact, about 50% of infarcted tissue was rescued by pre-treatment with AOL (FIG. 12).

Conclusion

These results extend, under ex vivo (living organ) conditions, the role of AOL as an inhibitor of mitochondrial ROS production, most probably at the level of complex I.

They also evidence the therapeutic interest of AOL for tissue protection against ischaemia/reperfusion damages, not only in heart but also in any tissue subjected to ischaemia.

Example 6: Effect of AOL in a Cardiovascular Disease: Cardiac Toxicity of Anthracyclines The present study aims at evaluating the effect of AOL in a model of cardiac toxicity of anthracyclines. This was assessed by administering anthracycline-derived anti-cancer drugs, together with AOL, to 10 week old rats for 14 to 17 days.

Material and Methods

The studies were performed on Sprague-Dawley rats aged 10 weeks and different treatments were administered intraperitoneally for 14 to 17 days, before collection of the heart for analysis. To respect the "three Rs principle" in animal experimentation, the number of group tested was limited as much as possible, in particular by focusing the experiments on one anthracycline molecule only, namely Doxorubicine, and by comparing the effect of AOL to one alternative protective molecule only, namely Dexrazoxane.

At the end of the experiment, the heart of the rats treated will be removed and cardiac function will be studied exhaustively after perfusion of these hearts in a Langendorhf system to determine the function cardiac affected by doxorubicin and whether AOL treatment is efficient.

The study comprises 5 different groups for 8 rats each:
1—Control group. Rats received the vehicle only, composed of 5% DMSO+95% NaCl 0.9%, twice a day (morning and evening) for 17 days;
2—Doxo group. Rats received Doxorubicine at a dose of 3 mg/kg (ip), every two days (morning), from day 3, for 14 days. Rats received vehicle only for every other injections;
3—Dexra group. Rats were treated with Dexrazoxane (reference protecting agent) at a dose of 30 mg/kg ip simultaneously with Doxorubicin at a dose of 3 mg/kg ip (according to the dosage ratio recommended by the French Regional Health Agency "ARS" in 2011), every two days, from day 3, for 14 days. Rats received vehicle only for every other injections;
4—AOL group. Rats were treated with AOL and Doxorubicin:
  4 mg/kg ip of AOL, mornings and evenings, for 72 hours preceding the first injection of Doxorubicin;
  on the days of Doxorubicin injection (based on the Doxo group): 4 mg/kg ip AOL together with the Doxorubicin injection, followed 90 minutes later by a second injection of AOL at a dose of 4 mg/kg ip;
  on the days without Doxorubicin injection: 4 mg/kg ip of AOL, mornings and evenings.
5—AOL/Carv/Enal group. Rats were treated similarly than rats from the AOL group here above. AOL injections were supplemented with a classical treatment for cardiac insufficiency (Carvediol, a β-blocker, at a dose of 1 mg/kg, and Enalapril, a vasodilator, at a dose of 0.5 mg/kg).

Example 7: Effect of AOL in in a Cardiovascular Disease: Pulmonary Hypertension

The present study aims at studying the role of mitochondria in the pulmonary vasculature physiology and providing a new alternative treatment of pulmonary hypertension. This disease is characterized by increased pulmonary arterial pressure and remodeling of pulmonary arteries (PA), leading to increased pulmonary vascular resistance, hypertrophy of the right ventricle, right heart failure and ultimately, death.

Pulmonary hypertension can be divided into five groups, among which the group 1 corresponds to pulmonary arterial hypertension. As for group 3, it includes pulmonary hypertension due to lung diseases (such as chronic obstructive pulmonary disorder) and/or alveolar hypoxemia.

To address the issue of the effect of AOL, two different rat models were used: a hypoxia model and a monocrotaline-induced model, that share pathophysiological characteristics with group 3 and group 1 pulmonary hypertension, respectively.

Material and Methods

Male Wistar rats (300-400 g) were separated into 3 groups and used 4 weeks later:
- the first group (control or normoxic rats—N rats) was housed in ambient room air;
- the second group (chronic hypoxic rats—CH rats) was exposed to chronic hypoxia for 3 weeks in a hypobaric chamber (50 kPa), and
- the third group (MCT rats) was injected with a single intraperitoneal dose of monocrotaline at a dose of 60 mg/kg. MCT (Sigma, St Quentin Fallavier, France) was dissolved in an equal volume of HCl (1 M) and NaOH (1 M).

In each group, some animals were treated with AOL (Sulfarlem, EG Labo Eurogenerics. Crushed tablets mixed with food, fed ad libitum) and some other animals were untreated. Eaten food was weighed every day to estimate the AOL dose administered. 10 mg/kg/day was thus administered during the 3 weeks of experiment for the second and third groups.

For each condition, 7 to 10 rats were used. All animal care and experimental procedures complied with the recommendations of the Federation of European Laboratory Animals Science Association, and were approved by the local ethics committee (Comite d'éthique régional d'Aquitaine—referenced 50110016-A).

Pulmonary hypertension was assessed by measuring both the mean pulmonary arterial pressure (mPAP) and right ventricle hypertrophy. To measure PAP, N, CH and MCT rats were anesthetized with pentobarbital sodium (Centravet) by intraperitoneal injection (60 mg/kg) and mPAP was measured, in closed-chest rats, through a catheter inserted in the right jugular vein, then through the right atria and the right ventricle into the pulmonary artery, and attached to a Baxter Uniflow gauge pressure transducer.

Right ventricle hypertrophy was estimated by the ratio of right ventricle (RV) to left ventricle plus septum (LV+S) weight (Fulton index).

Pulmonary arteries (PA) remodeling was assessed by measuring the percentage of the PA medial thickness from sections of paraffin-embedded lung. Lung sections were first stained with hematoxylin and eosin (VWR) according to common histological procedure. On each section, three groups of 10 intracinar arteries with different cross-sectional diameters were observed to evaluate medial wall thickness (namely cross-sectional diameters under 50 µm, between 50 to 100 µm and between 100 to 150 µm).

Results

Figure 13A:
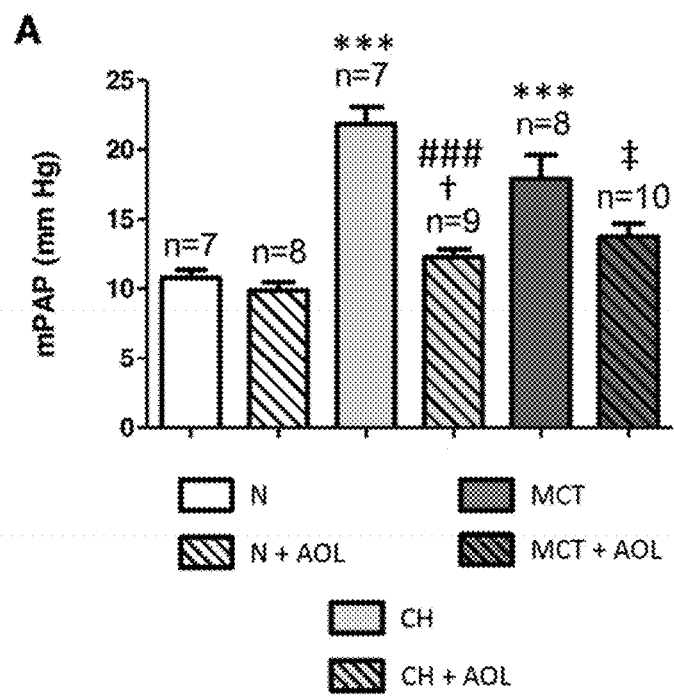
FIG. 13A: effect of AOL (hatched columns) on the mean pulmonary arterial pressure (mPAP) measured in normoxic rats (N, white columns), chronic hypoxic rats (CH, light grey columns) and monocrotaline-treated rats (MCT, dark grey columns) n is the number of rats. *,  and * indicate a significant difference for P<0.05, 0.01 and 0.0001 respectively versus N. ### indicates a significant difference for P<0.05 versus CH. † and †† indicate a significant difference for P<0.05 and 0.01 respectively versus N+AOL. ‡ indicates a significant difference for P<0.05 versus MCT.
Figure 13B:
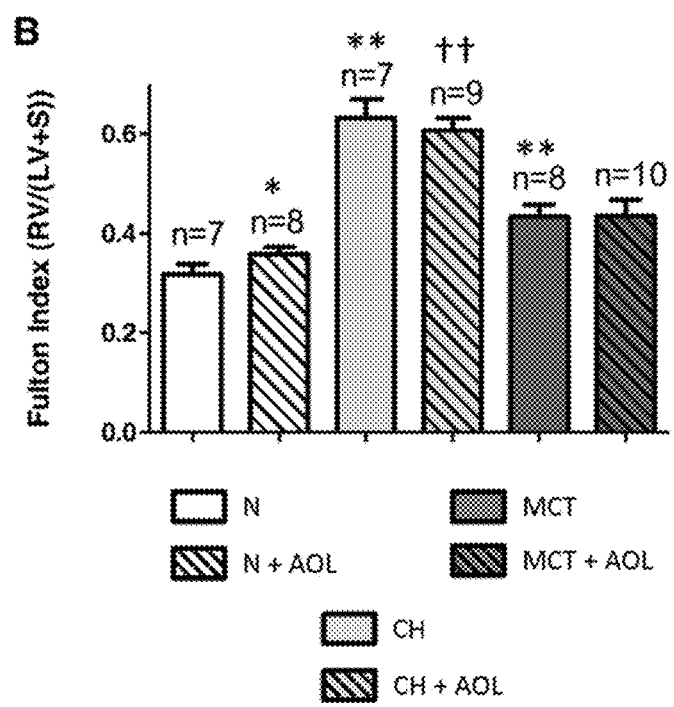
FIG. 13B: right ventricular hypertrophy expressed as the Fulton index (i.e., ratio of right ventricle weight (RV) to left ventricle plus septum weight (LV+S)). n is the number of rats. *,  and * indicate a significant difference for P<0.05, 0.01 and 0.0001 respectively versus N. ### indicates a significant difference for P<0.05 versus CH. † and †† indicate a significant difference for P<0.05 and 0.01 respectively versus N+AOL. ‡ indicates a significant difference for P<0.05 versus MCT.

Results are expressed as mean±SEM of n independent observations. All data were analyzed using a non-parametric test for unpaired samples (Mann-Whitney test). FIG. 13 shows the effect of AOL on pulmonary arterial pressure (FIG. 13A) and heart remodeling (FIG. 13B). n indicates the number of rats for mPAP and Fulton index measurements. All bar graphs and statistics were performed with Graphpad PRISM software (v6, Graphpad Software). P<0.05 were considered significant. As seen, AOL had no significant effect on the control group (N rats). However, mean pulmonary arterial pressure was decreased in MCT rats treated with AOL, and even more significantly in CH rats treated with AOL. AOL treatment had however no effect on the Fulton index.

Figure 14A:
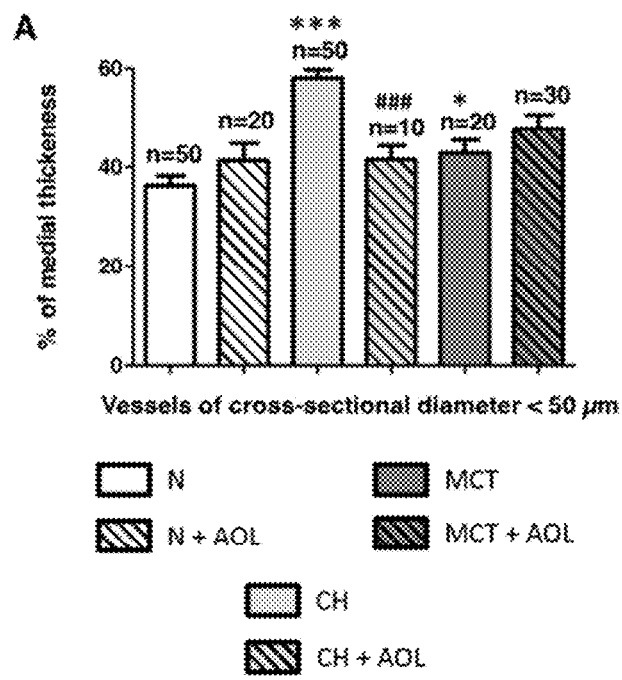
FIG. 14A: PA medial thickness assessed in rats with intraacinar arteries of cross-sectional diameter under 50 n is the number of vessels. *,  and * indicate a significant difference for P<0.05, 0.01 and 0.0001 respectively versus N. ## and ### indicate a significant difference for P<0.01 and 0.0001 versus CH. a significant difference for P<0.05 and 0.01 respectively versus N+AOL. ‡ indicates a significant difference for P<0.05 versus MCT.
Figure 14B:
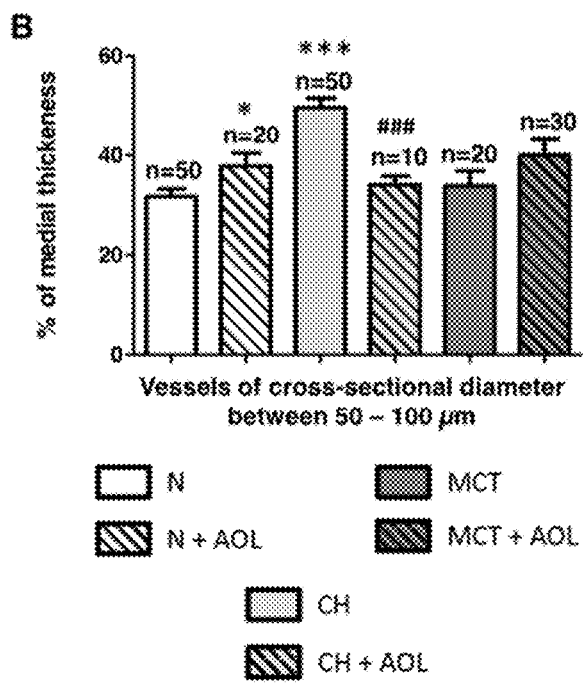
FIG. 14B: PA medial thickness assessed in rats with intraacinar arteries of cross-sectional diameter between 50 to 100 μm. n is the number of vessels. *,  and * indicate a significant difference for P<0.05, 0.01 and 0.0001 respectively versus N. ## and ### indicate a significant difference for P<0.01 and 0.0001 versus CH. a significant difference for P<0.05 and 0.01 respectively versus N+AOL. ‡ indicates a significant difference for P<0.05 versus MCT.
Figure 14C:
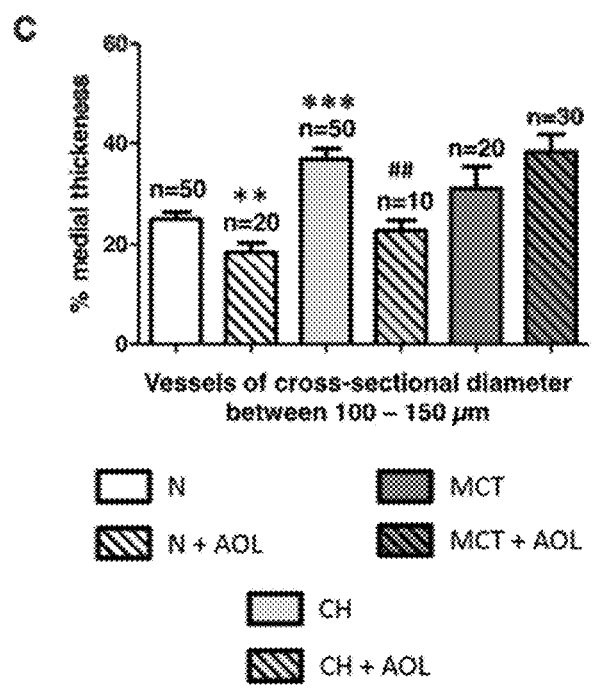
FIG. 14C: PA medial thickness assessed in rats with intraacinar arteries of cross-sectional diameter between 100 to 150 n is the number of vessels. *,  and * indicate a significant difference for P<0.05, 0.01 and 0.0001 respectively versus N. ## and ### indicate a significant difference for P<0.01 and 0.0001 versus CH. a significant difference for P<0.05 and 0.01 respectively versus N+AOL. ‡ indicates a significant difference for P<0.05 versus MCT.

FIG. 14 shows the effect of AOL on pulmonary arteries remodeling. n indicates the number of vessels analyzed for % of medial thickness measurement. All bar graphs and statistics were performed with Graphpad PRISM software (v6, Graphpad Software). P<0.05 were considered significant. AOL shows a significant effect in CH rats, in which pulmonary arteries diameter was reduced by 30%.

Conclusion

AOL treatment, at an oral dose of 10 mg/kg/day, has a significant effect in the prevention and/or treatment of pulmonary hypertension in vivo, in particular in group 3 pulmonary hypertension. Results indeed show a significant improvement of clinical symptomatology.

These data suggest that mitochondria play a major role in the pulmonary vasculature physiology, and extend the use of AOL to the treatment of pulmonary hypertension.

Example 8: Effect of AOL in Aging Disease and Progeroid Syndromes: Macular Degeneration The present study aims at evaluating the capacity for AOL to protect retina against progressive degeneration.

Material and Methods

Rats bred under cyclic low-intensity lighting were transferred to cyclic high-intensity lighting for one week and divided into 3 groups (non-treated animals, vehicle-treated animals and AOL-treated animals). Treated animals received injections of vehicle or AOL at a dose of 6 mg/kg/day, three times a day for the 7 days of the transfer (30 minutes before light-ON; at 01.00 µm; at 09.00 µm). After one week, animals were transferred in the dark (D0).

A control group ("untransferred") was not transferred to cyclic high-intensity lighting but received the same treatment as described above: injections of vehicle or AOL three times a day for 7 days, followed by a transfer in the dark (D0).

On the day following the transfer in the dark (D1), a first electroretinography is performed. It measures the electrophysiological signal which is generated by the retina, in response to a light stimulation. It is typically characterized by two waves, namely a-wave and b-wave. a-wave represents the initial corneal-negative deflection, derived from the cones and rods of the outer photoreceptor layers. It reflects the hyperpolarization of the photoreceptors due to closure of sodium ion channels in the outer-segment membrane. b-wave represents the corneal-positive deflection, derived from the inner retina (predominantly Muller and ON-bipolar cells). Analysis of the electroretinogram consists in measuring the amplitude and/or latency of these waves, as a function of the intensity of the light stimulation. a-wave amplitude, for a given light stimulation intensity, depends on the number of photoreceptors; whereas amplitude of b-wave, for a given light stimulation intensity and a given number of photoreceptors, indicates the signal transmission efficiency.

After D1's electroretinography, animals were transferred back under cyclic low-intensity lighting conditions, and a second electroretinography is performed at D15.

Animals were then sacrificed for histological analysis. The thickness of the various layers of the retina, in particular the thickness of the outer nuclear layer (ONL) and inner nuclear layer (INL) were measured (in µm, from the optical nerve and every 0.39 mm in the superior and inferior poles of the optic disc).

Results

Figure 15A:
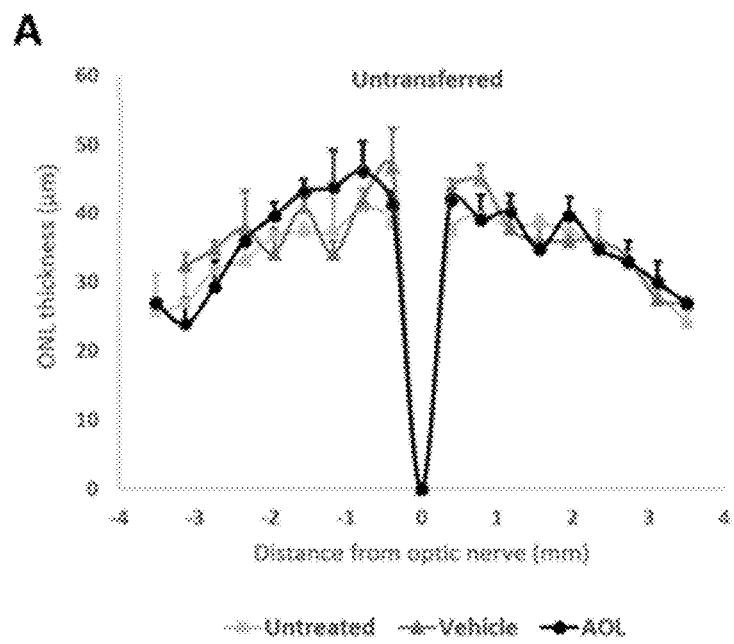
FIG. 15A: effect of vehicle and AOL on "untransferred" animals. Animals were bred under cyclic low-intensity lighting and received injections of vehicle or AOL three times a day for 7 days. Fifteen days after the end of the treatment, histological analysis of the retina was carried out. Data are expressed as mean±SEM thickness of the ONL, for untreated animals (light grey, square dots), vehicle-treated animals (dark grey, triangle dots) and AOL-treated animals (black, round dots), in μm, from the optical nerve and every 0.39 mm in the superior and inferior poles of the optic disc.

Histological analysis is reported on FIG. 15. It shows that, in the control group ("untransferred"), treatment with AOL has no effect on ONL's thickness (FIG. 15A). This suggests that AOL does not have a toxic effect on retina's photoreceptors.

Figure 15B:
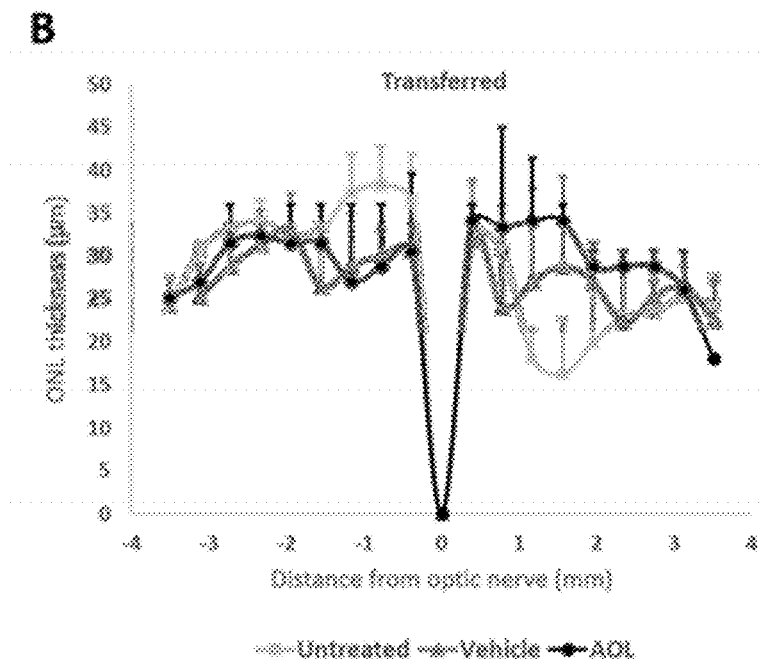
FIG. 15B: effect of vehicle and AOL on "transferred" animals. Animals were bred under cyclic low-intensity lighting and transferred to cyclic high-intensity lightning for 7 days, during which they received injections of vehicle or AOL three times a day. At the end of the treatment, animals were transferred back under cyclic low-intensity lighting conditions, and histological analysis of the retina was carried out fifteen days later. Data are expressed as mean±SEM thickness of the ONL, for untreated animals (light grey, square dots), vehicle-treated animals (dark grey, triangle dots) and AOL-treated animals (black, round dots), in μm, from the optical nerve and every 0.39 mm in the superior and inferior poles of the optic disc.

On the contrary, transfer in cyclic high-intensity lighting conditions ("transferred") induces a significant decrease (by half in some areas) of the ONL, in non-treated animals. AOL however tends to protect the ONL against light-induced damages. Histological analysis has indeed shown a significant increase of the thickness of the ONL in AOL-treated/cyclic high-intensity lighting-exposed animals (FIG. 15B).

Conclusion

AOL treatment has a significant protective effect against light-induced damages on the retina. In particular, the thickness of the retina was shown to be preserved as compared to non-treated animals, after prolonged cyclic high-intensity lighting exposure.

Example 9: Effect of AOL in Diseases Related to Mitochondrial Dysfunctions

The present study aims at testing the effect of AOL in vivo, in a model of oxidative phosphorylation dysfunction.

Material and Methods

Mice deficient in mitochondrial Mn-Superoxide Dismutase (Sod2-KO) on a CD1-background were used. This genetic alteration leads to an adverse phenotype and the death of animals at an average of 8 days old. Mitochondrial superoxide dismutase is a free radical scavenging enzyme which transforms superoxide (highly reactive) into hydrogen peroxide (less reactive), that could then cross mitochondrial membranes and be detoxified by matrix and cytosolic anti-oxidant systems. The aim of this study was to test if AOL could rescue the Sod2-KO phenotype through its activity on $I_Q$ superoxide production.

After birth, pups were genotyped (3 day-old) and the litter size was reduced to 6 pups per cage. Animals were then treated (AOL in Kolliphor®-5 mg/kg) or not (Kolliphor® only, noted KOL below). The choice of the dosage was mainly driven by the solubility limit of the compound (2.8 mM in Kolliphor®) and the maximum injectable volume in pups (6 to 7 µL per gram body mass). Two studies were conducted on two different generations from the same parents: lifespan; and succinate dehydrogenase activity in heart (SDH) and Oil Red O staining in liver. Animals were weighed and injected (intra-peritoneal) daily.

Succinate dehydrogenase activity is a marker of superoxide in the mitochondrial matrix. Thus, a lack of SOD2 is associated with a decrease of SDH activity in heart. The aim of this experiment was to test whether or not AOL could restore SDH activity in KO mice.

Oil Red O staining is a marker of lipid that has been shown to accumulate in Sod2-KO liver. However, the direct link between superoxide/hydrogen peroxide production and liver lipid accumulation is not established. The aim of the study was to test the potency of AOL to prevent liver lipid accumulation in Sod2-KO mice.

Results

Lifespan 4 groups were constituted:
1—WT-KOL (n=7), a group of wild-type mice treated with the vehicle only,
2—WT-AOL (n=17), a group of wild-type mice treated with AOL,
3—KO-KOL (n=2), a group of Sod2-KO mice treated with the vehicle only,
4—KO-AOL (n=4), a group of Sod2-KO mice treated with AOL.

Animals were injected once a day from 3 days old until their death.

Figure 16A:
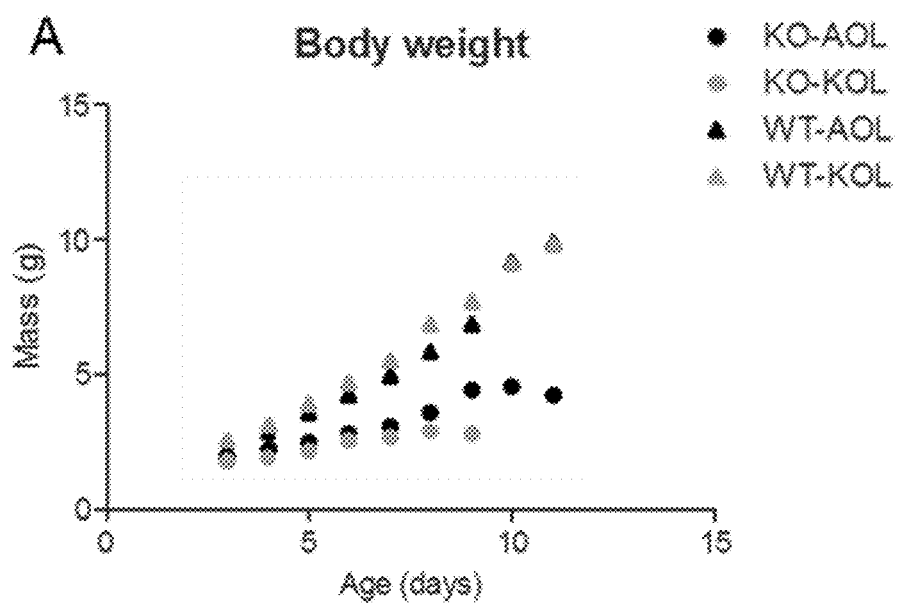
FIG. 16A: evolution of mice body weight, in grams over time, in days.
Figure 16B:
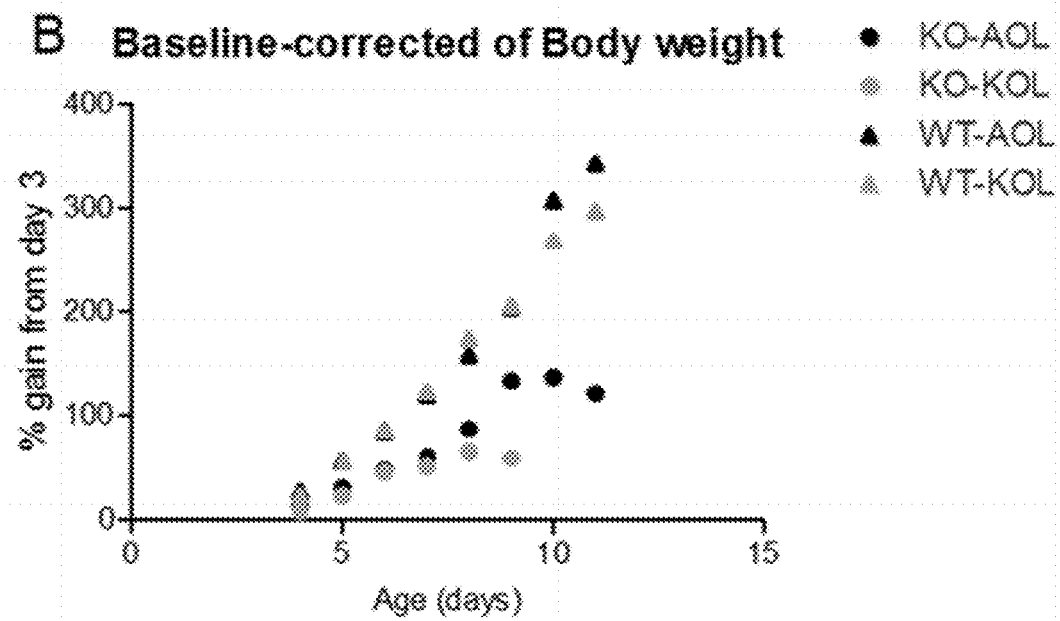
FIG. 16B: baseline-corrected of mice body weight, as a percentage of weight gain over time, in days.

FIG. 16A and FIG. 16B show the evolution of body weight (A) and percentage of initial body weight. These results show that body weight and body weight gain were lower in KO-mice than in WT-mice. Treatment with AOL however tends to alleviate this effect as seen from day 8 to 12, suggesting a potential beneficial effect of the compound.

Figure 16C:
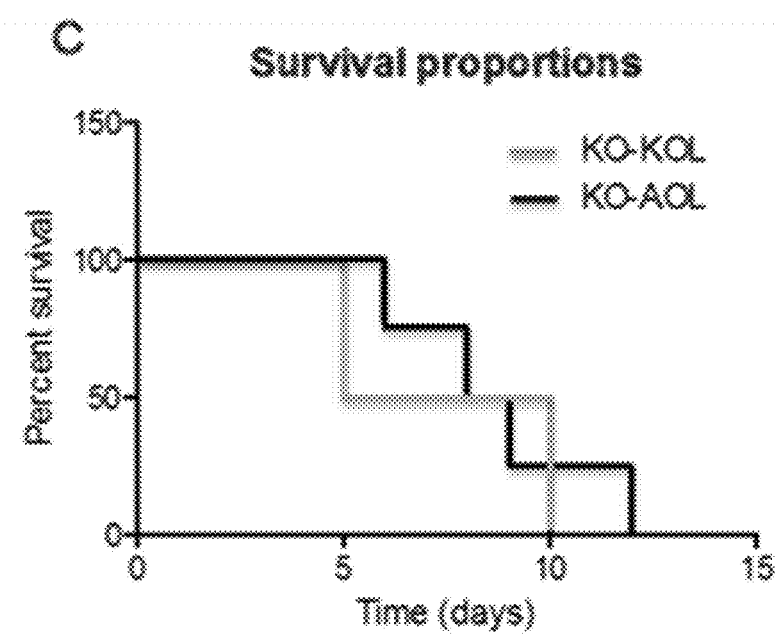
FIG. 16C: survival proportion among the KO-KOL and KO-AOL groups, in percentage over time, in days.

FIG. 16C shows the survival proportion of Sod2-KO mice whether they were treated with AOL or not. As expected in view of the above results, both median lifespan and maximal lifespan were slightly improved by AOL treatment in KO mice, with AOL-treated mice living up to 2 days longer as compared to untreated mice, supporting a beneficial effect of AOL.

SDH Activity in Heart & Oil Red O Staining 5 groups were constituted:
1—WT-non-injected (n=6), a group of untreated wild-type mice;
2—WT-KOL (n=6), a group of wild-type mice treated with the vehicle only;
3—WT-AOL (n=6), a group of wild-type mice treated with AOL;
4—KO-KOL (n=4), a group of Sod2-KO mice treated with the vehicle only;
5—KO-AOL (n=6), a group of Sod2-KO mice treated with AOL.

In this study, animals were treated daily (5 mg/kg) from day 3 to day 5. Heart and liver were harvested at day 6.

Figure 17:
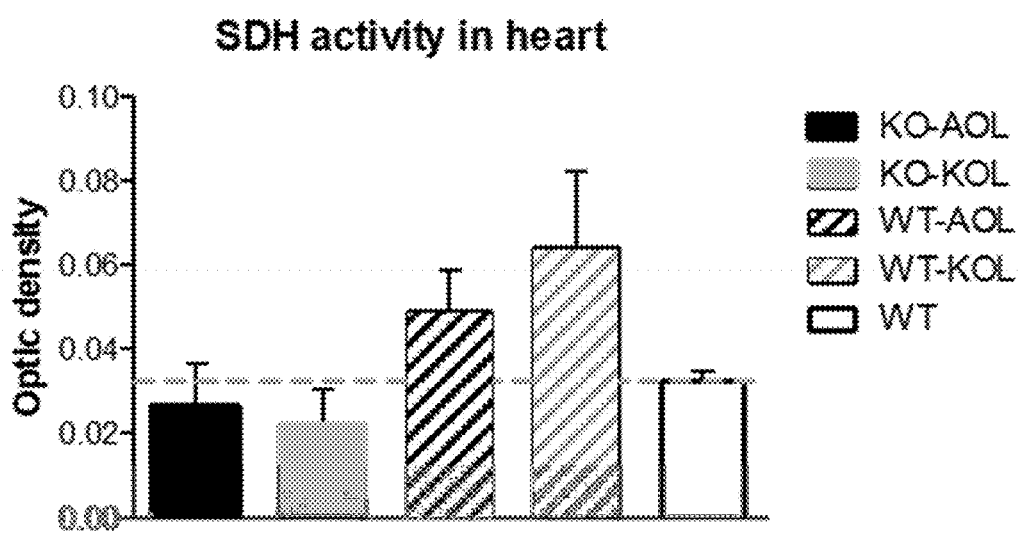
FIG. 17 is a graph showing the succinate dehydrogenase (SDH) activity in heart, among five groups of mice (WT-KOL: wild-type mice treated with vehicle; WT-AOL: wild-type mice treated with AOL; KO-KOL: SOD2-KO mice treated with vehicle; KO-AOL: SOD2-KO mice treated with AOL; WT: wild-type untreated mice). The optical density of SDH reaction sampled from heart sections was measured with the image processing software Image Analyst MKII (Akos). This density was expressed in the form of mean grey level where mean grey level=sum of grey/number of pixels measured. Data are expressed as mean values of the measured optical density.

As expected, SDH activity tended to decrease (not significant) in KO compared to WT animals. However, AOL showed only a very slight increase in SDH activity in KO mice, but could not restore SDH activity to the levels of WT mice (FIG. 17).

Figure 18A:
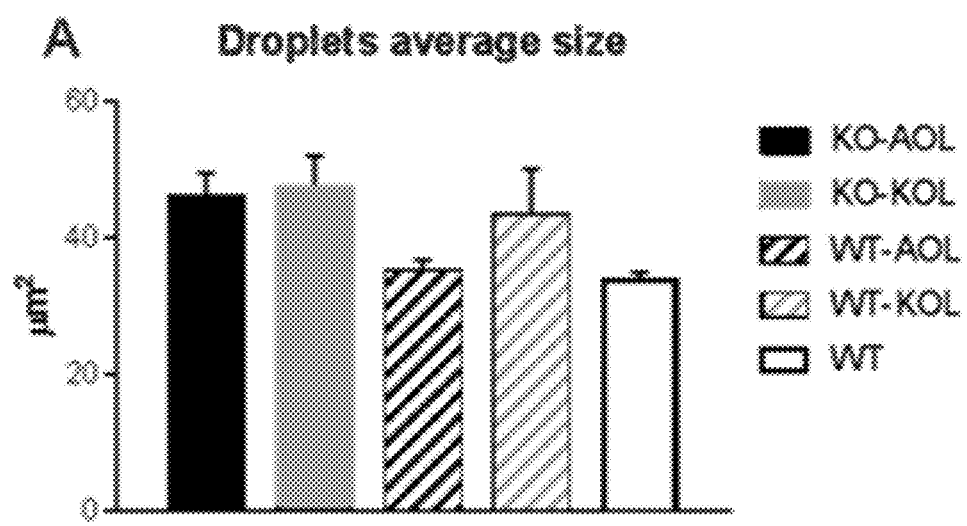
FIG. 18A: Average size of lipids droplets.
Figure 18B:
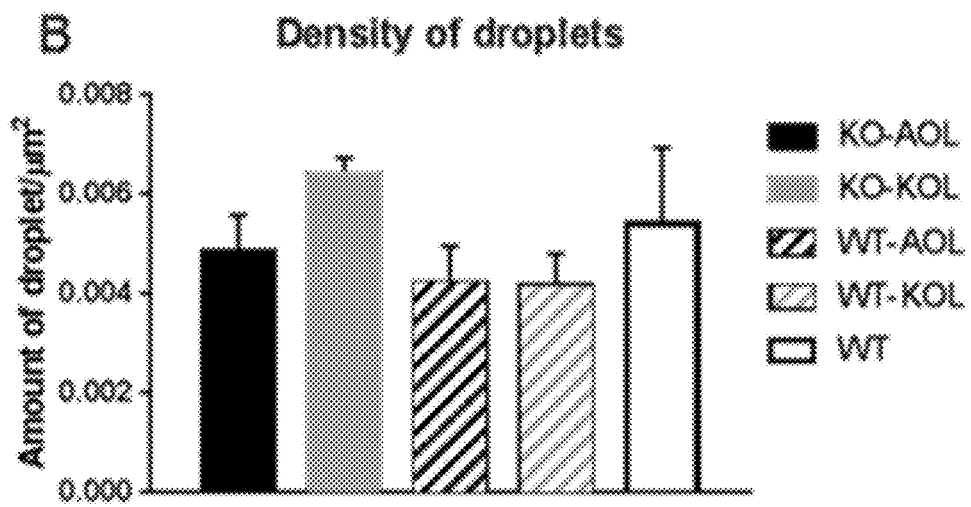
FIG. 18B: droplet density (droplets number/liver area).
Figure 18C:
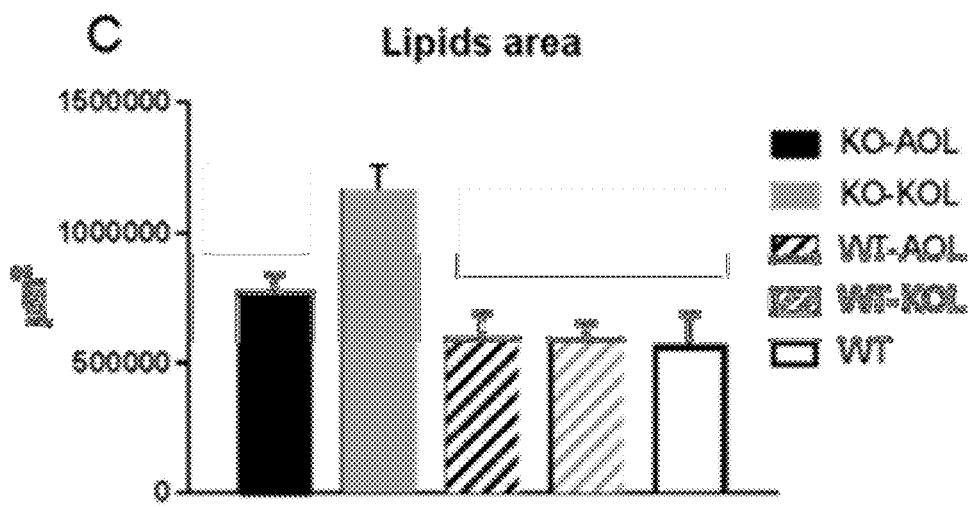
FIG. 18C: total lipid area (average size×droplets number).

FIG. 18 shows lipid droplets average size (Panel A), density (Panel B) and area (Panel C). Untreated KO mice exhibited a high lipid content phenotype compared to WT animals. In AOL-treated KO mice however, lipid droplets density decreased as compared to untreated animals. More importantly, these results also show that AOL treatment was able to restore the total lipid area in KO mice, consistent with on-target suppression of mitochondrial superoxide production in vivo in Sod2-KO mice.

Conclusion

In vivo studies show encouraging results. Although AOL treatment could not fully counteract the effects of SOD2 depletion in mice, results show that lifespan could still be extended by a couple of day as compared to untreated KO animals, together with an alleviation of the decrease in body weight gain. This suggests a potential effect of AOL.

AOL bioavailability is known to be very short. Thus, treatment with higher doses might lead to improve AOL effects in these experiments. However, constitutive KO remains a high adverse phenotype to rescue with only one very specific treatment and may require synergic action with other drugs.

In vivo, results also showed that AOL could restore lipid content and/or prevent lipid accumulation in liver of Sod2-KO mice.

Example 10: Effect of AOL in an Autoimmune Disease: Scleroderma

The present study aims at testing the effect of AOL on fibroblasts from patients with scleroderma. Scleroderma is a chronic systemic autoimmune disease characterized by an increased synthesis of collagen, damages to small blood vessels, activation of T lymphocytes and production of altered connective tissues.

Material and Methods

Fibroblasts from both a healthy donor and a patient with scleroderma are cultured in flasks, in complete DMEM medium (10% FCS, 1% antibiotic). After 6-hour adhesion, cells are deprived of serum overnight.

AOL is extemporaneously prepared. AOL was weighed and dissolved in DMSO at 5 mg/mL. This stock solution was further diluted to 10 and 5 mM final, in DMSO. AOL was further diluted in complete DMEM medium, to reach final concentrations of 40, 20 and 10 µM.

Cultured cells were contacted with AOL at 40, 20 and 10 µM. Control cells were contacted with complete DMEM medium, supplemented with DMSO (0.2%) and N-acetyl-cysteine (3 mM). Cells are incubated under normoxic conditions (37° C., 20% 02) and under hypoxia (37° C., 1% 02) for 6 or 24 hours.

For MMP-1, MIP and MCP secretion analysis, the culture supernatant is harvested, aliquoted and stored at −20° C. for dosage. MMP-1 is quantified by ELISA (Abcam), according to the manufacturer's instructions. MCP-1 and MIP-1α concentrations are quantified by CBA (Cytometric Bead Array, Biolegend).

For MMP1, collagen and CCl2 expression analysis, cells are detached with trypsin and washed with PBS. The cell pellet is then resuspended in lysis buffer, and RNA extraction is carried out according to the manufacturer's instructions (Nucleospin RNA Plus, Macherey Nagel). 1 µg of RNA is retro-transcribed (GoScript, Promega), then diluted 10-fold before SYBR Green qPCR (SYBR qPCR Premix Ex Taq, Takara) in a BioRad CFX384 PCR machine. Primers for MMP-1, Col1A2 and CCl2 are used to measure genes of interest; primers for Ppia, RPLP0 and EEF1A1 are used to measure reference genes.

The invention claimed is:

1. A method for treating or preventing free oxygen radicals-related liver diseases in a subject in need thereof, said method comprising administering to said subject an inhibitor of production of reactive oxygen species (ROS),
   wherein said inhibitor of production of ROS is anethole trithione, and
   wherein said free oxygen radicals-related liver disease is selected from the group consisting of diabetes, alcoholic fatty liver disease, non-alcoholic fatty liver disease, liver inflammation in hepatitis C and cirrhosis.

2. The method according to claim 1, wherein said free oxygen radicals-related liver disease is diabetes.

3. A method for increasing insulin secretion in a subject in need thereof, said method comprising administering to said subject an inhibitor of production of reactive oxygen species (ROS),
   wherein said inhibitor of production of ROS is anethole trithione.

4. The method according to claim 3, for increasing glucose-stimulated insulin secretion (GSIS).

5. The method according to claim 3, wherein the subject in need thereof is affected with an insulin secretion deficiency.

6. The method according to claim 3, wherein the subject in need thereof is affected with a free oxygen radicals-related liver disease selected from the group consisting of diabetes, alcoholic fatty liver disease, non-alcoholic fatty liver disease, liver inflammation in hepatitis C and cirrhosis.

7. The method according to claim 3, wherein the subject in need thereof is affected with diabetes.

8. A method for decreasing body weight and/or food intake in a subject in need thereof, said method comprising administering to said subject an inhibitor of production of reactive oxygen species (ROS),
   wherein said inhibitor of production of ROS is anethole trithione, and wherein decreasing body weight comprises decreasing fat mass and/or blood glucose levels in the subject in need thereof.

9. The method according to claim 8, wherein the subject in need thereof is affected with a free oxygen radicals-related liver disease selected from the group consisting of diabetes, alcoholic fatty liver disease, non-alcoholic fatty liver disease, liver inflammation in hepatitis C and cirrhosis.

10. The method according to claim 8, wherein the subject in need thereof is affected with dietary obesity.

* * * * *